US012742781B2

(12) United States Patent
Kang et al.

(10) Patent No.: US 12,742,781 B2
(45) Date of Patent: Sep. 22, 2026

(54) DIAGNOSIS METHOD FOR BLADDER CANCER

(71) Applicants: LSI Medience Corporation, Tokyo (JP); KYUSHU UNIVERSITY, NATIONAL UNIVERSITY CORPORATION, Fukuoka (JP)

(72) Inventors: Dongchon Kang, Fukuoka (JP); Takeshi Uchiumi, Fukuoka (JP); Ko Igami, Fukuoka (JP)

(73) Assignees: LSI Medience Corporation, Tokyo (JP); Kyushu University, National University Corporation, Fukuoka (JP)

( * ) Notice: Subject to any disclaimer, the term of this patent is extended or adjusted under 35 U.S.C. 154(b) by 661 days.

(21) Appl. No.: 18/040,306

(22) PCT Filed: Aug. 6, 2021

(86) PCT No.: PCT/JP2021/029360

§ 371 (c)(1),
(2) Date: Feb. 2, 2023

(87) PCT Pub. No.: WO2022/030626

PCT Pub. Date: Feb. 10, 2022

(65) Prior Publication Data

US 2023/0266323 A1 Aug. 24, 2023

(30) Foreign Application Priority Data

Aug. 6, 2020 (JP) ................................ 2020-133478

(51) Int. Cl.
*G01N 33/575* (2026.01)
*G01N 33/68* (2006.01)

(52) U.S. Cl.
CPC ....... *G01N 33/57557* (2026.01); *G01N 33/68* (2013.01); *G01N 2800/52* (2013.01)

(58) Field of Classification Search
CPC ....................... G01N 33/57407; G01N 33/574
See application file for complete search history.

(56) References Cited

U.S. PATENT DOCUMENTS

| | | | |
|---|---|---|---|
| 2010/0196426 | A1 | 8/2010 | Skog et al. |
| 2017/0234880 | A1 | 8/2017 | Zeng |
| 2017/0350902 | A1 | 12/2017 | Lin et al. |
| 2018/0327852 | A1 | 11/2018 | Murakami et al. |
| 2018/0372754 | A1 | 12/2018 | Garin et al. |

FOREIGN PATENT DOCUMENTS

| | | | |
|---|---|---|---|
| CN | 105891500 | A | 8/2016 |
| CN | 109762899 | A | 5/2019 |
| JP | 201591251 | A | 5/2015 |
| JP | 5838963 | B2 | 1/2016 |
| JP | 2017526916 | A | 9/2017 |
| JP | 2018533368 | A | 11/2018 |
| JP | 2019215342 | A | 12/2019 |
| WO | 2016143805 | A1 | 9/2016 |
| WO | 2020071489 | A1 | 4/2020 |

OTHER PUBLICATIONS

American Cancer Society (Bladder Cancer Stages, https://www.cancer.org/cancer/types/bladder-cancer/detection-diagnosis-staging/staging.html, downloaded Dec. 3, 2025, p. 1-11) (Year: 2025).*

Akaza et al. "Evaluation of Urinary NMP22 (Nuclear Matrix Protein 22) as a Diagnostic Marker for Urothelial Cancer. NMP22 as a Urinary Marker for Surveillance of Bladder Cancer", Japanese Journal of Cancer and Chemotherapy, vol. 24, No. 7, pp. 829-836. Japanese Language. May 1997.

Castanheira de Oliveira et al., "Urinary Biomarkers in Bladder Cancer: Where Do We Stand and Potential Role of Extracellular Vesicles", Cancers, vol. 12, No. 1400, pp. 1-30. 2020.

Clancy et al., "Regulated Delivery of Molecular Cargo to Invasive Tumour-Derived Microvesicles", Nature Communications, pp. 1-11. Apr. 21, 2015.

Fernandez-Llama et al., "Tamm-Horsfall Protein and Urinary Exosome Isolation", Kidney International, vol. 77, pp. 736-742. Feb. 3, 2010.

International Search Report and Written Opinion in International Application No. PCT/JP2021/029360, with partial translation. Oct. 26, 2021.

Jemal et al., "Cancer Statistics, 2007", CA Cancer J. Clin., vol. 57, pp. 43-66. 2007.

Lee et al., "Altered Proteome of Extracellular Vesicles Derived from Bladder Cancer Patients Urine", Molecure Cells, vol. 41(3), pp. 179-187. Mar. 9, 2018.

Takashi et al.. "Bladder Cancer Marker (Urinary BTA, Urinary NMP22)", Rinsho Kensa Gaido 2001-2002, pp. 945-947. Japanese Language. 2001.

Takashi et al., "Use of Diagnostic Categories in Urinary Cytology in Comparison wiht the Bladder Tumour Antigen (BTA) Test in Bladder Cancer Patients", International Urology and Nephrology, vol. 31, No. 2, pp. 189-196. 1999.

Timaner et al., "Microparticles from Tumors Exposed to Radiation Promote Immune Evasion in Part by PD-L1", Oncogene, vol. 39, pp. 187-203. 2020.

Wiener et al., "Accuracy of Urinary Cytology in teh Diagnosis of Primary and Recurrent Bladder Cancer", Acta Cytologica, pp. 163-169. Jul. 7, 1992.

Zieger et al., "Long-Term Follow-Up of Noninvasive Bladder Tumours (stage Ta): Recurrence and Progression", BJU International, vol. 85, pp. 824-828. 2000.

Supplementary Partial European Search Report in EP Application No. 21854475, 17 pages. Aug. 2, 2024.

Chen et al., "Comparative and Targeted Proteomic Analyses of Urinary Microparticles from Bladder Cancer and Hernia Patients", Journal of Proteome Research, vol. 11, pp. 5611-5629. 2012.

(Continued)

*Primary Examiner* — Peter J Reddig
(74) *Attorney, Agent, or Firm* — Heslin Rothenberg Farley & Mesiti P.C.

(57) ABSTRACT

Substances present in urinary microvesicles of bladder cancer patients are identified to thereby construct a method of assisting in early and accurate diagnosis of bladder cancer. In the assistant method, microvesicles are enriched, and whether or not the subject patient has bladder cancer is determined depending on the amount of a marker protein present in the microvesicles.

8 Claims, 19 Drawing Sheets

(56) References Cited

OTHER PUBLICATIONS

Smalley et al., "Isolation and Identification of Potential Urinary Microparticle Biomarkers of Bladder Cancer", Journal of Proteome Research, vol. 7, pp. 2088-2096. 2008.
Extended European Search Report in European Application No. 21854475.7, 20 pages. Nov. 13, 2024.
Dankner et al., "CEACAM1 as a Multi-Purpose Target for Cancer Immunotherapy", Oncoimmunology, vol. 6, No. 7, 16 pages. Jun. 28, 2017.
Igami et al., "Extracellular Vesicles Expressing CEACAM Proteins in the Urine of Bladder Cancer Patients", Cancer Science, vol. 113, pp. 3120-3133. May 24, 2022.
Igami et al., "Abstract 5104: Extracellular Vesicles Expressing CEACAM Proteins in the Urine of Bladder Cancer Patients", Poster Presentations—Proffered Abstracts, 5 pages. Jun. 15, 2022.
Tilki et al., "CEACAM1: A Novel Urinary Marker for Bladder Cancer Detection", European Urology, vol. 57, pp. 648-654. May 28, 2009.

* cited by examiner

[Figure 1]
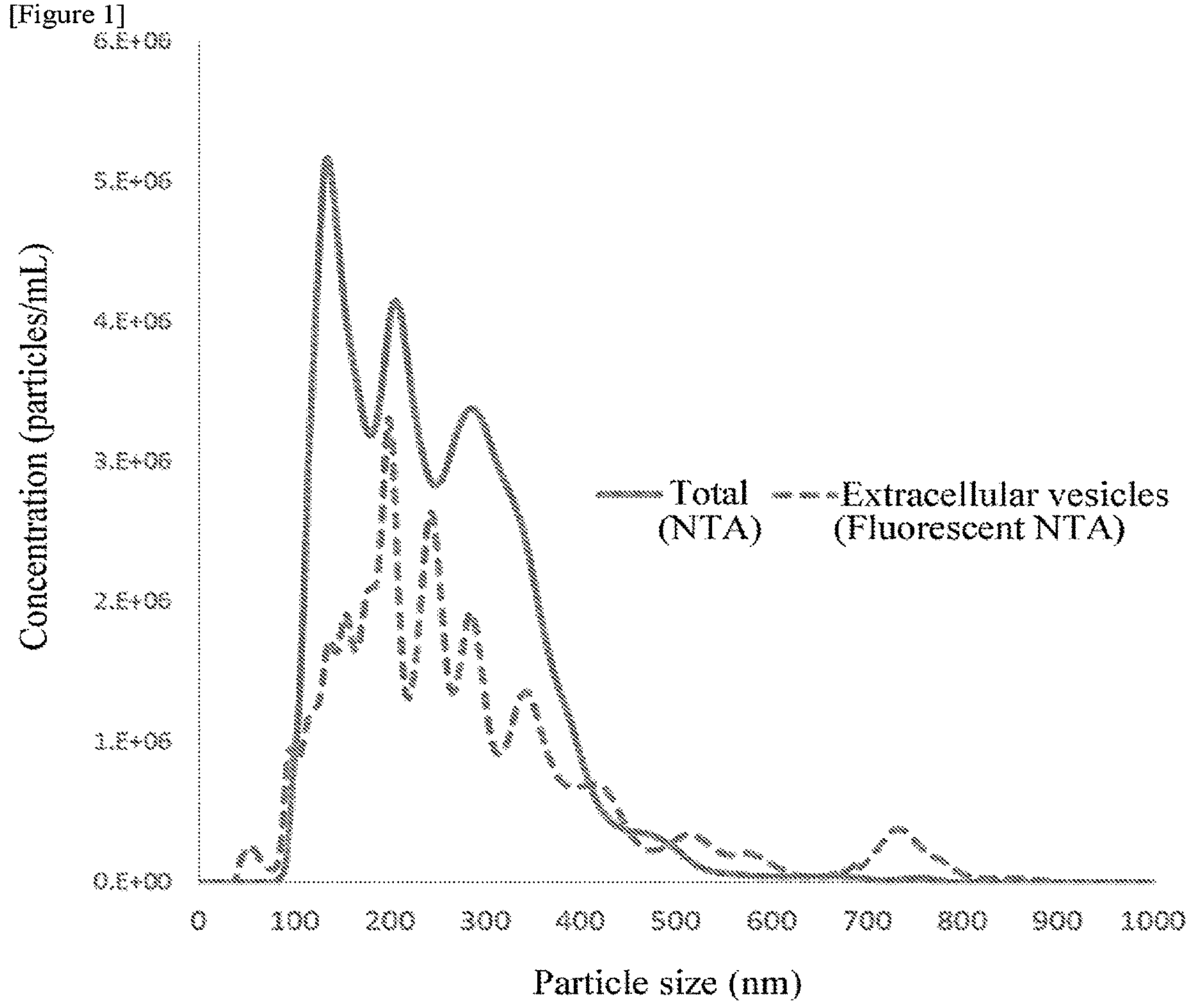

[Figure 2]
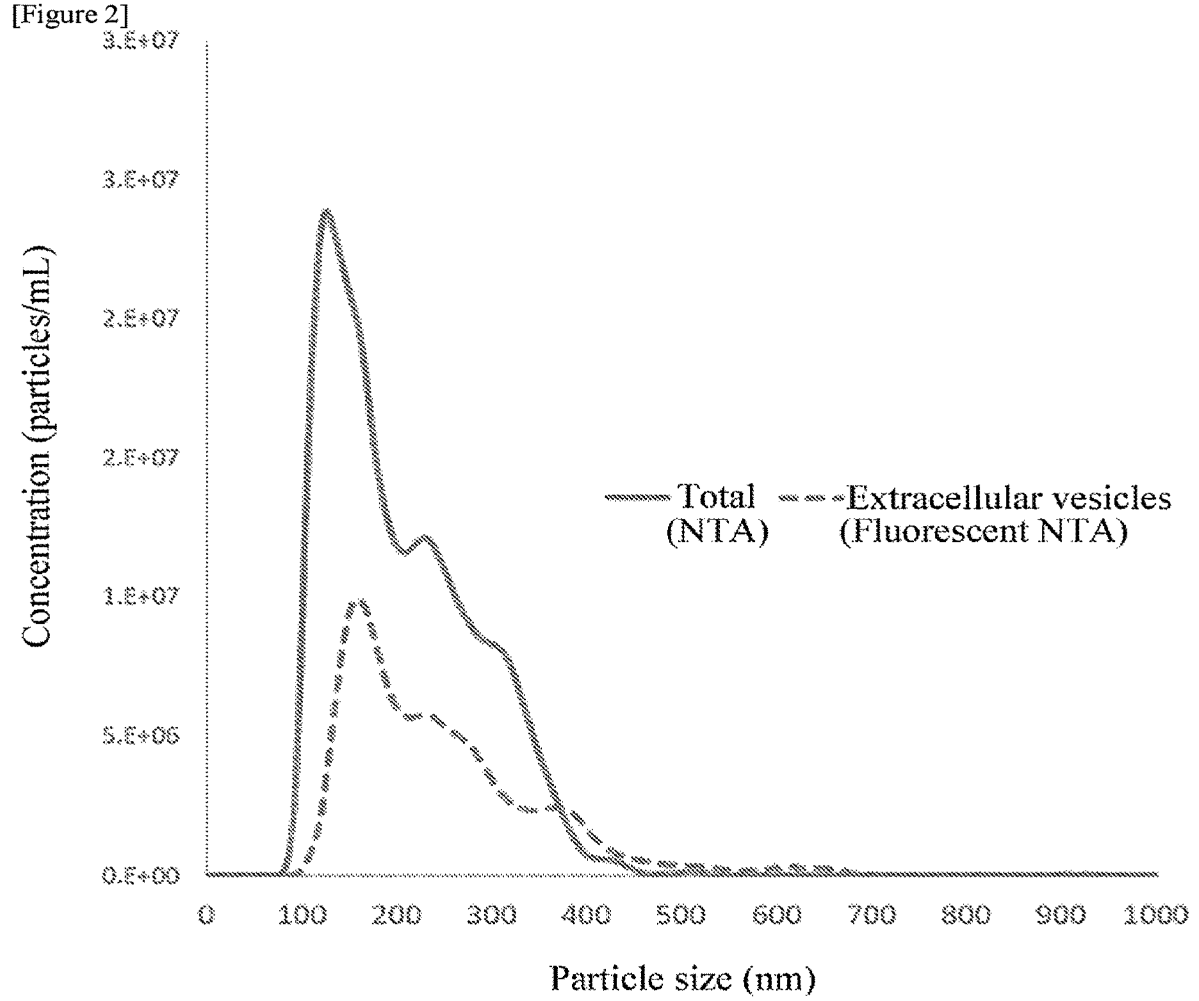

[Figure 3]
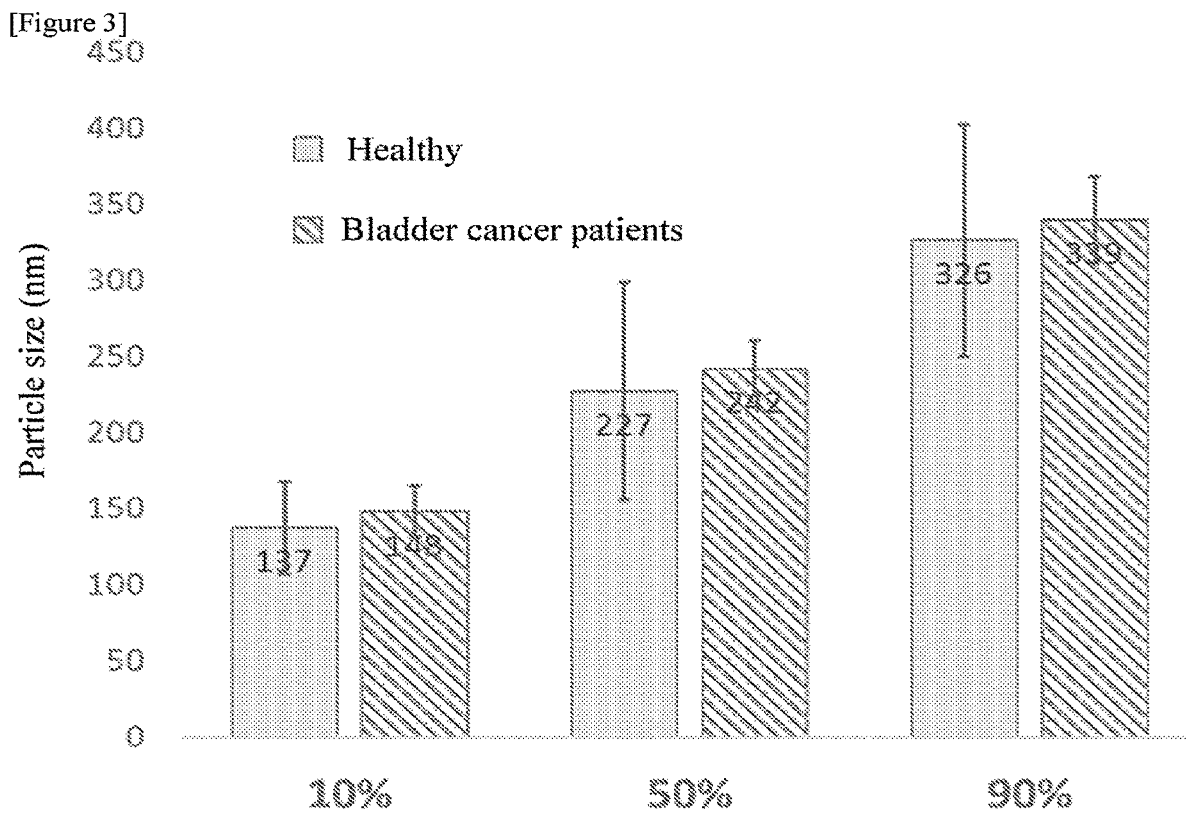
[Figure 4]
Bladder cancer patients
Healthy
585
749
644

[Figure 5]

| GO | Category | Description | Count | Log10(P) |
|---|---|---|---|---|
| R-HSA-156842 | Reactome Gene Sets | Eukaryotic Translation Elongation | 39 | -41.0 |
| ko04610 | KEGG Pathway | Complement and coagulation cascades | 33 | -34.6 |
| GO:0045055 | GO Biological Processes | regulated exocytosis | 73 | -27.7 |
| R-HSA-109582 | Reactome Gene Sets | Hemostasis | 55 | -19.7 |
| GO:0002253 | GO Biological Processes | activation of immune response | 58 | -18.0 |
| GO:0043062 | GO Biological Processes | extracellular structure organization | 43 | -16.4 |
| GO:0007229 | GO Biological Processes | integrin-mediated signaling pathway | 20 | -13.4 |
| GO:0072378 | GO Biological Processes | blood coagulation, fibrin clot formation | 12 | -13.1 |
| GO:0052547 | GO Biological Processes | regulation of peptidase activity | 37 | -12.2 |
| CORUM:3062 | CORUM | DGCR8 multiprotein complex | 8 | -11.4 |
| GO:0034330 | GO Biological Processes | cell junction organization | 29 | -10.9 |
| WP3888 | WikiPathways | VEGFA-VEGFR2 Signaling Pathway | 34 | -10.8 |
| GO:0030155 | GO Biological Processes | regulation of cell adhesion | 45 | -10.5 |
| R-HSA-382551 | Reactome Gene Sets | Transport of small molecules | 43 | -9.6 |
| GO:0050900 | GO Biological Processes | leukocyte migration | 35 | -9.5 |
| GO:0022618 | GO Biological Processes | ribonucleoprotein complex assembly | 25 | -9.4 |
| R-HSA-381426 | Reactome Gene Sets | Regulation of Insulin-like Growth Factor (IGF) transport and uptake by Insulin-like Growth Factor Binding Proteins | 17 | -9.3 |
| GO:0042730 | GO Biological Processes | fibrinolysis | 9 | -9.2 |
| GO:0034113 | GO Biological Processes | heterotypic cell-cell adhesion | 12 | -8.6 |
| WP411 | WikiPathways | mRNA Processing | 18 | -8.4 |

[Figure 6]
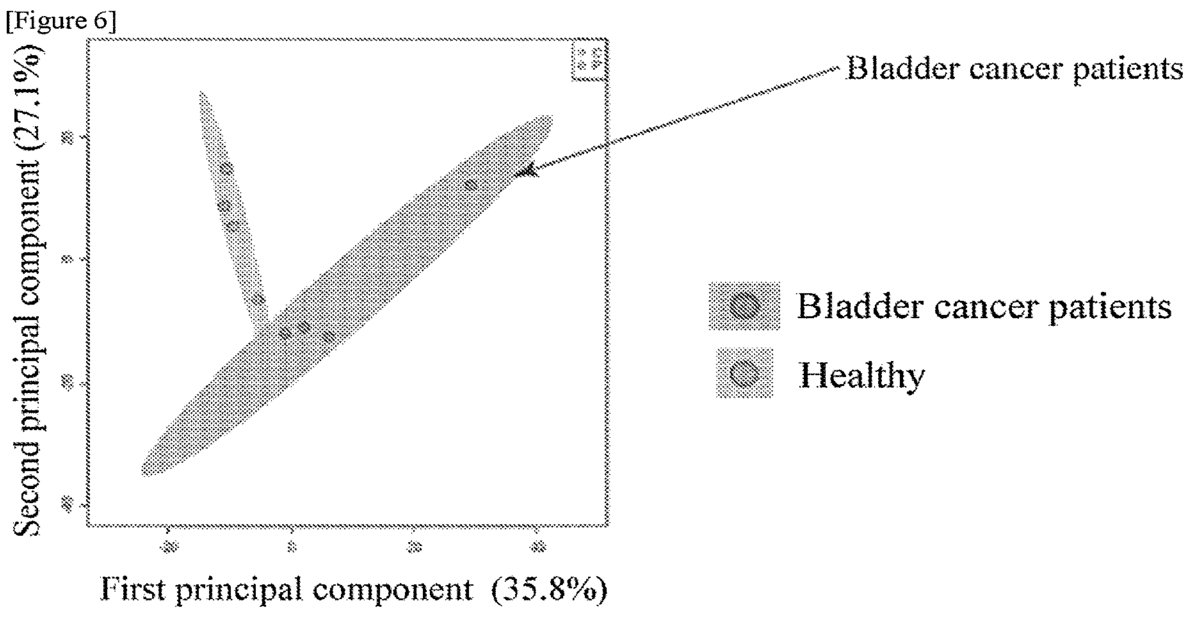
[Figure 7]
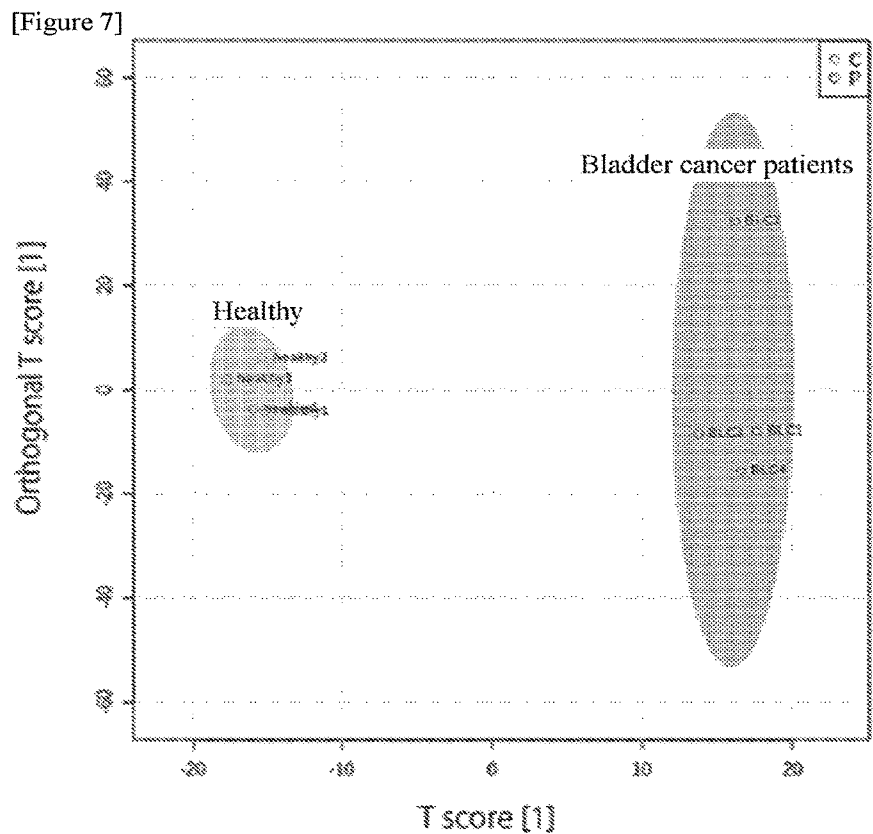

[Figure 8]
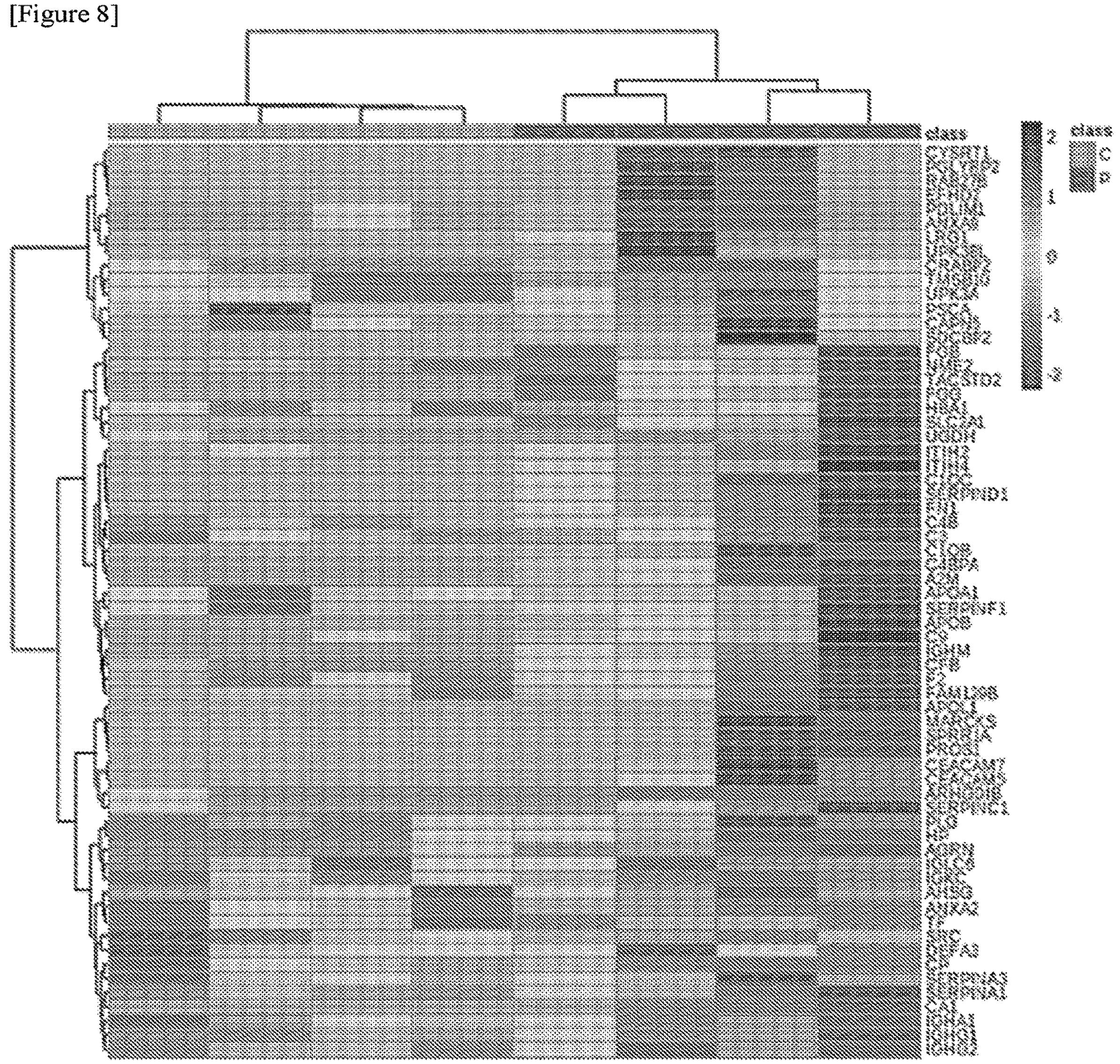

[Figure 9]
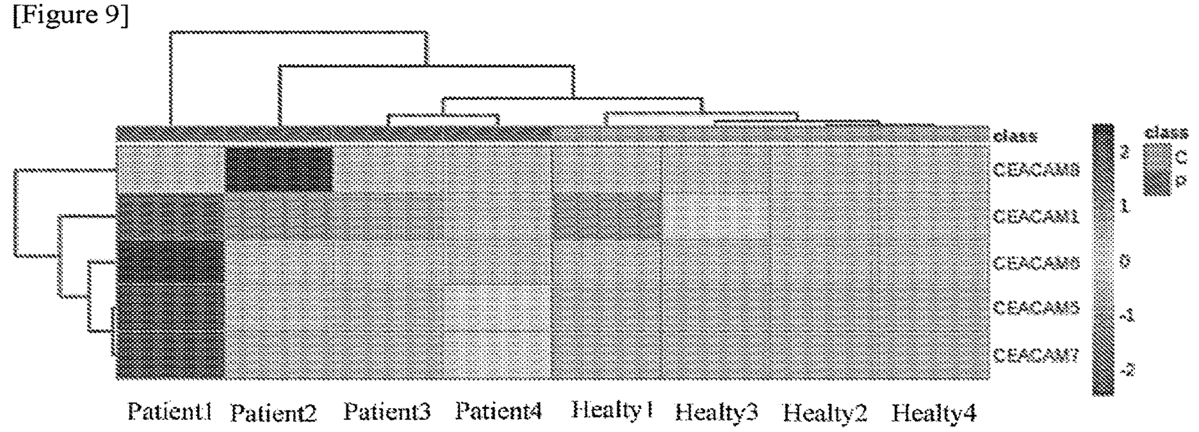
[Figure 10]
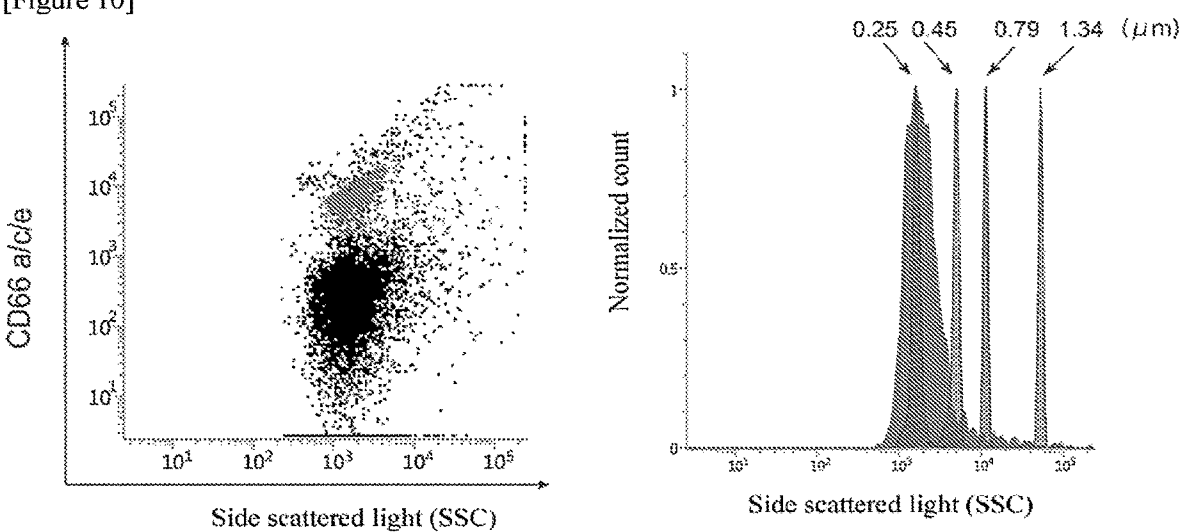

[Figure 11]
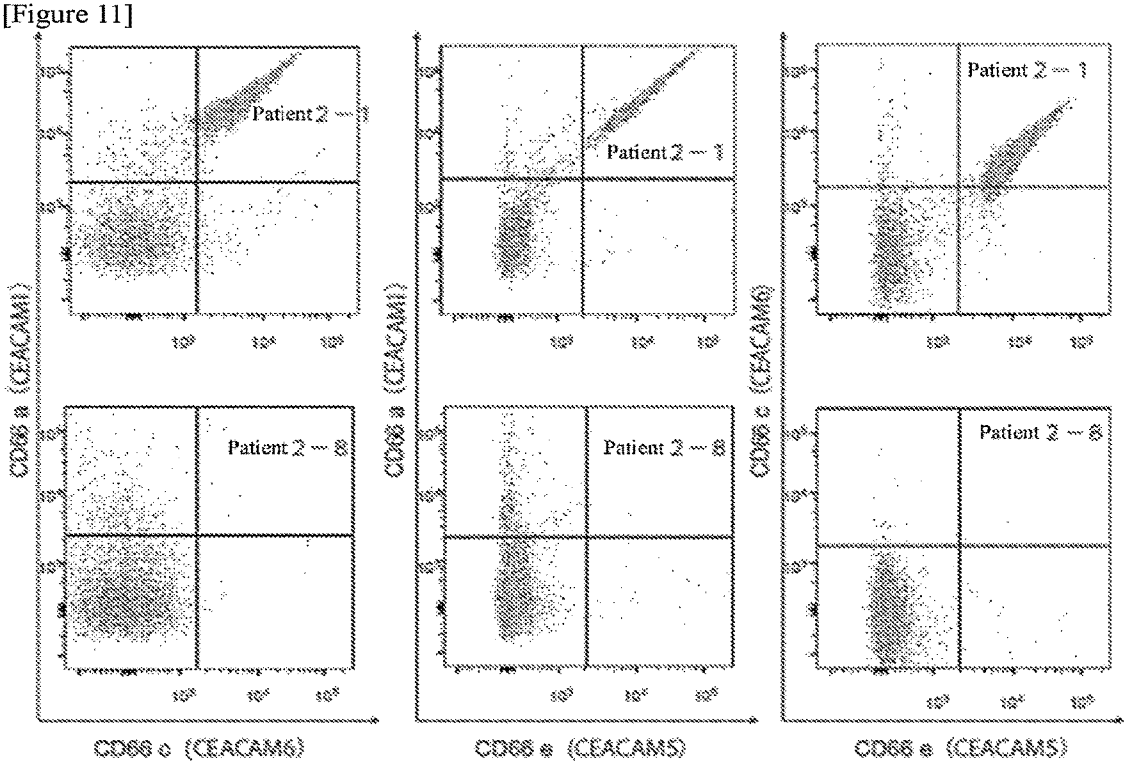
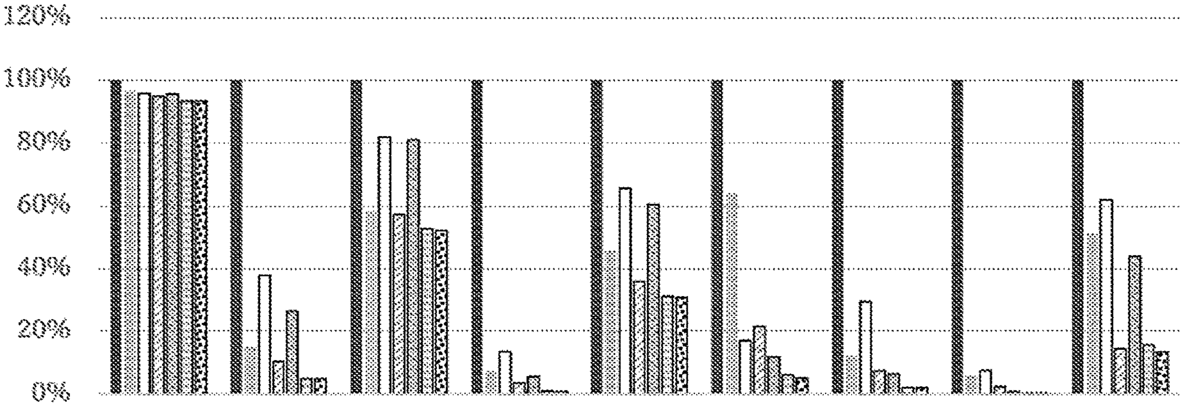

[Figure 12]
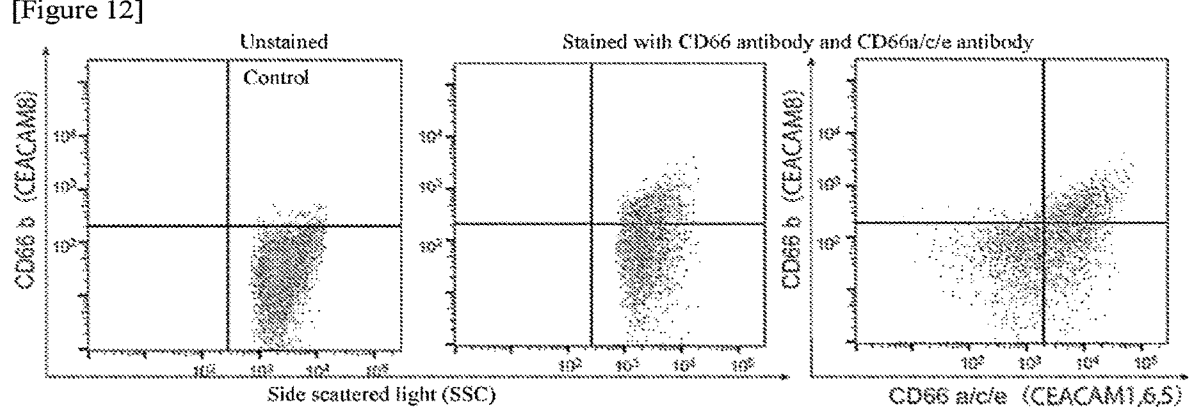

[Figure 13]
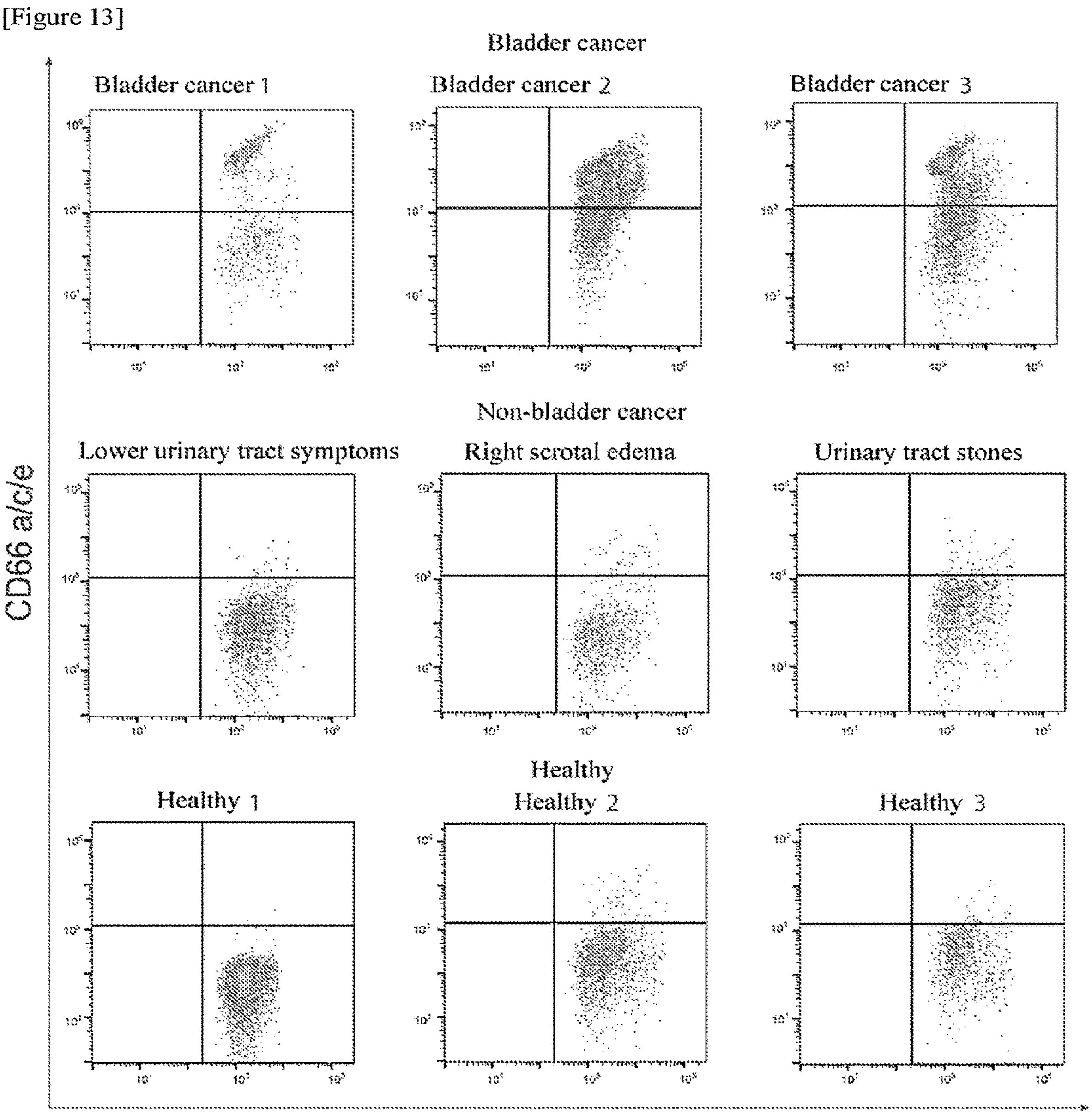

[Figure 14]
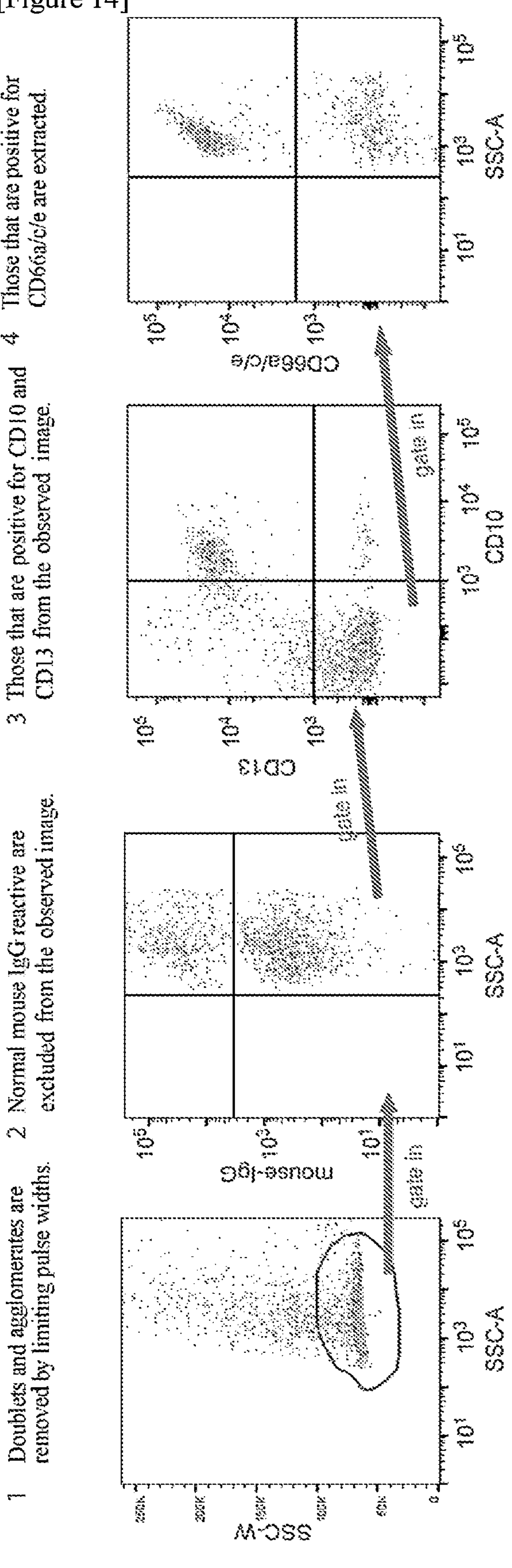

[Figure 15]
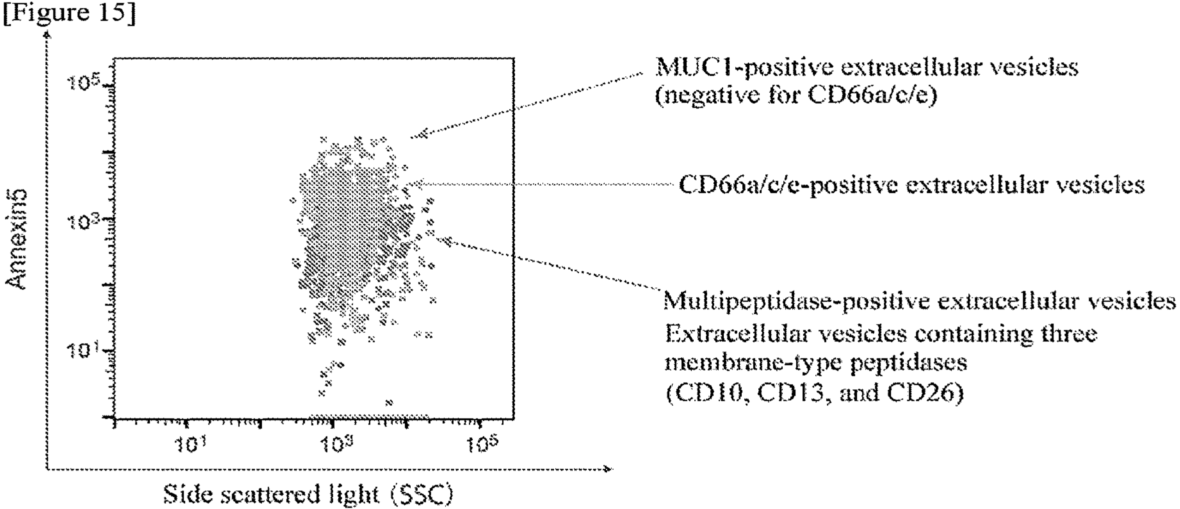
[Figure 16]
The extracellular vesicles positive for CD66a/c/e in bladder cancer patients are different from those positive for CD26.
CD66 a/c/e
CD26

[Figure 17]
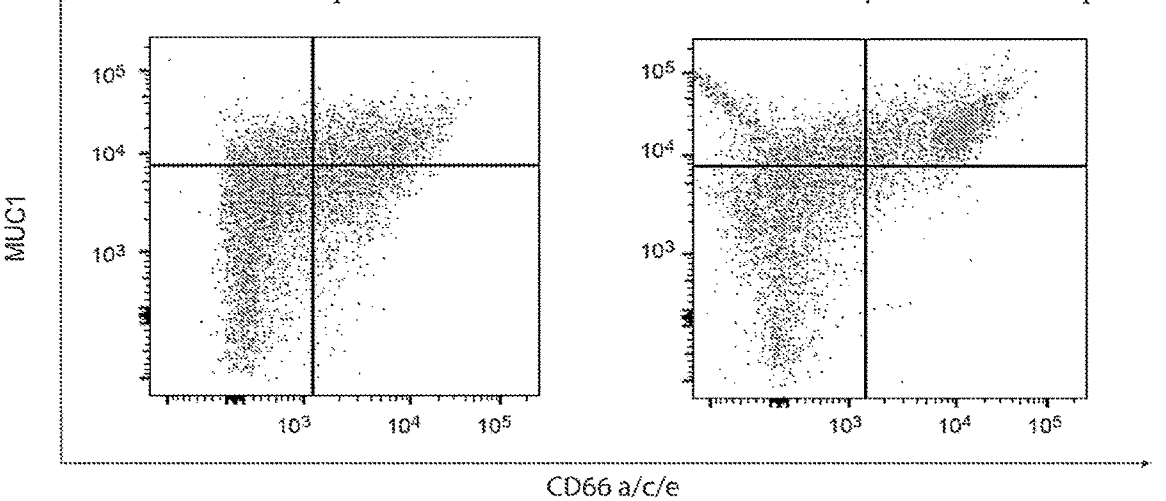

[Figure 19]
CD66 a/c/e
Percentage of positive fraction in observed image (%)
* p< 0.05
Healthy Non-bladder cancer Bladder cancer
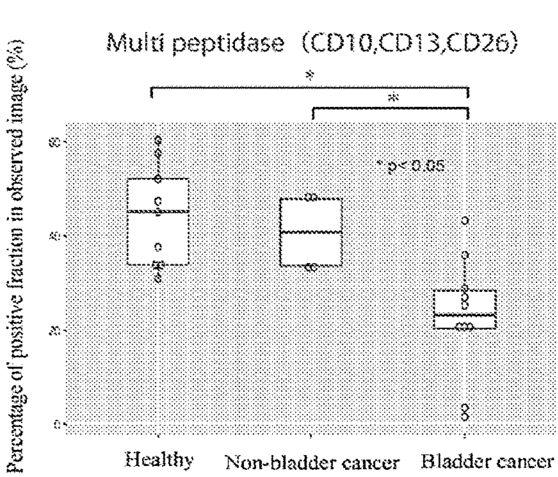
[Figure 20]
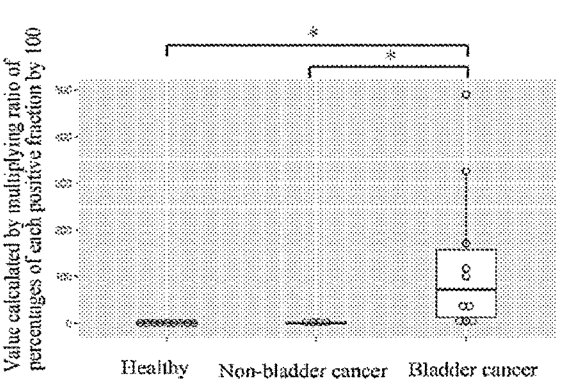
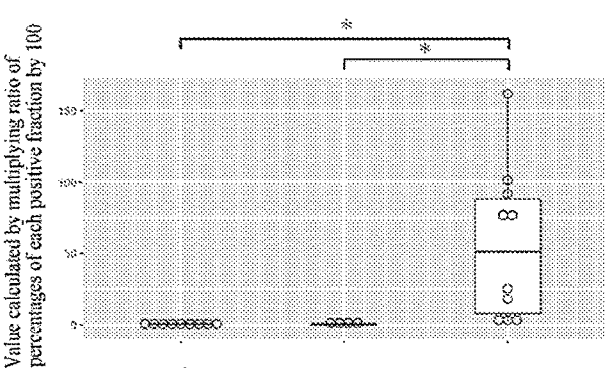

[Figure 21]

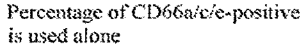

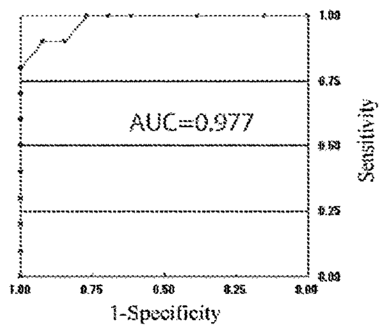

Cut-off: 0.81% CD66ace+

| | | Bladder cancer | | |
|---|---|---|---|---|
| | | − | + | Total |
| CD66a/c/e positive | − | 12 | 1 | 13 |
| | + | 1 | 9 | 10 |
| | Total | 13 | 10 | |

Sensitivity 90%
Specificity 92%

Ratio of percentage of CD66a/c/e-positive to percentage of multipeptidase-positive

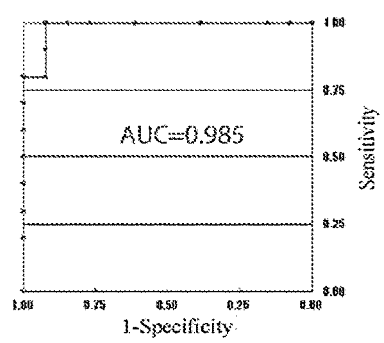

Cut-off: 1.6 CD66ace+/Multipeptidase*100

| | | Bladder cancer | | |
|---|---|---|---|---|
| | | − | + | Total |
| Ratio(CD66a/c/e positive / Multipeptidase) | − | 12 | 0 | 12 |
| | + | 1 | 10 | 11 |
| | Total | 13 | 10 | |

Sensitivity 100%
Specificity 92%

Ratio of percentage of CD66a/c/e-positive to percentage of multipeptidase positive and MUC1 positive (negative for CD66a/c/e)

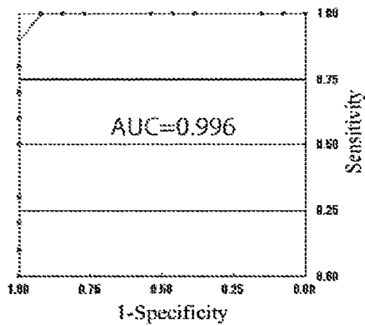

Cut-off: 1.4 CD66ace*100 /(Multipeptidase+MUC1)

| | | Bladder cancer | | |
|---|---|---|---|---|
| | | − | + | Total |
| Ratio(CD66a/c/e positive / Multipeptidase) | − | 12 | 0 | 12 |
| | + | 1 | 10 | 11 |
| | Total | 13 | 10 | |

Sensitivity 100%
Specificity 92%

[Figure 22]
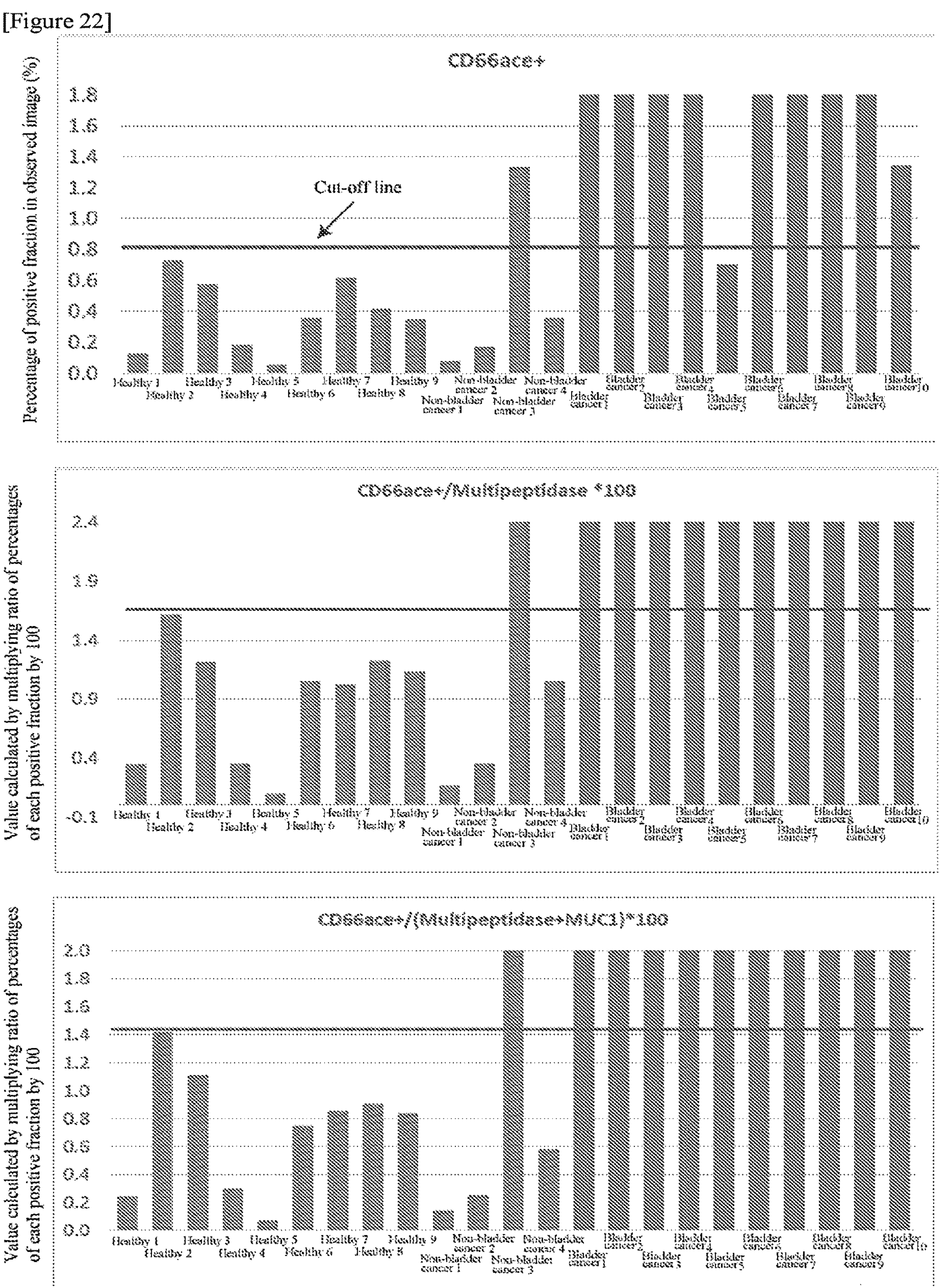

[Figure 23]
1.
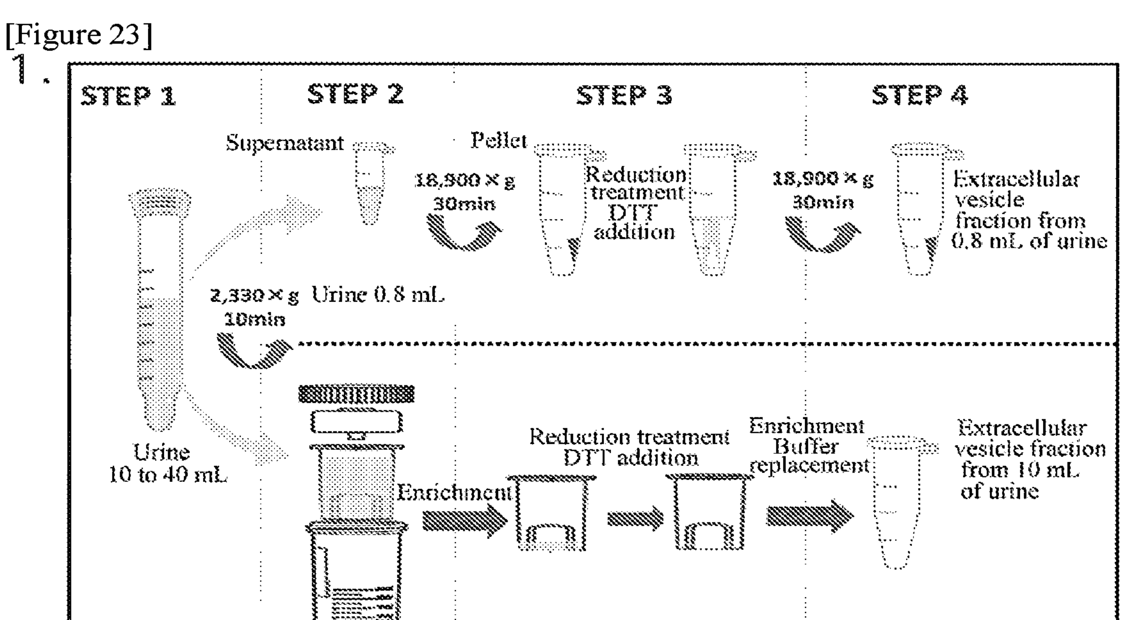
2.
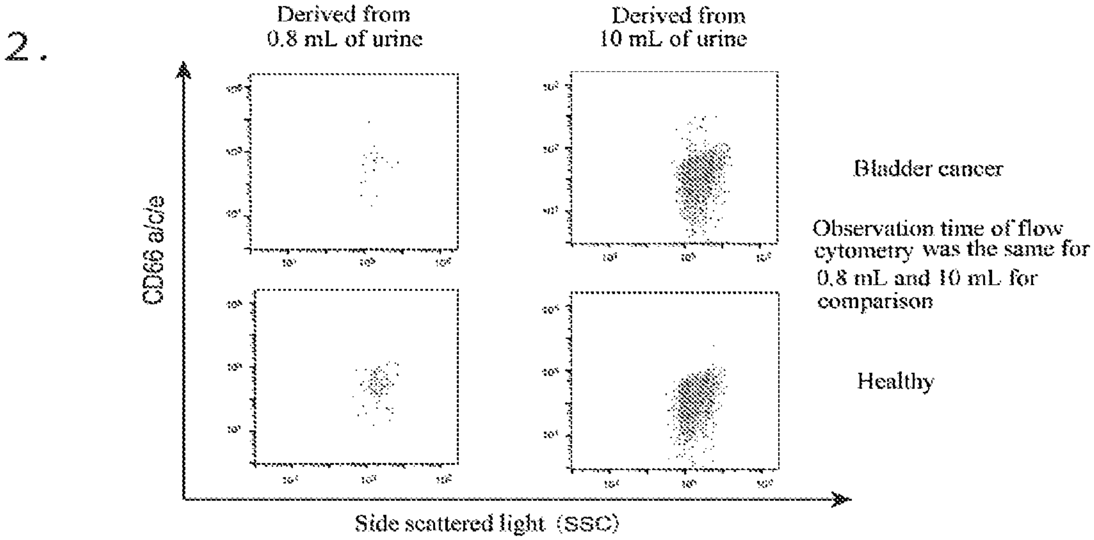
3.
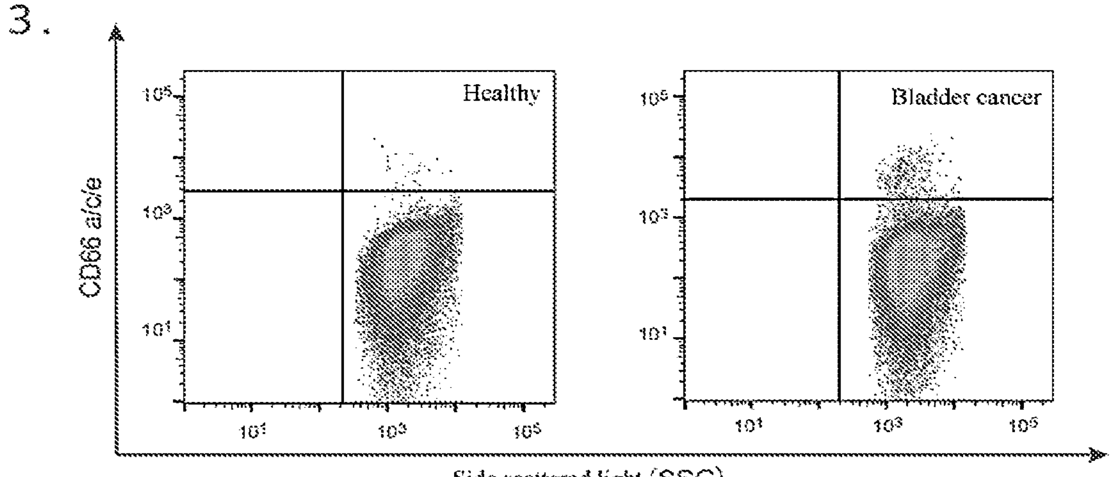

[Figure 24]
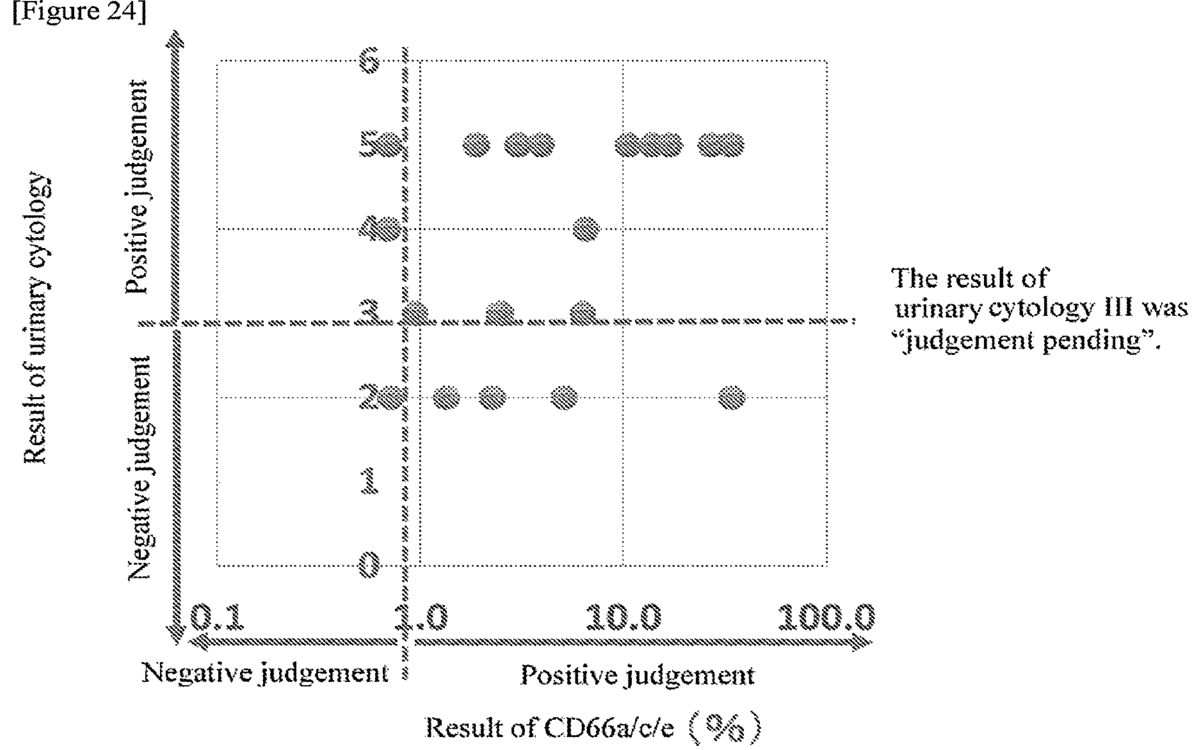

DIAGNOSIS METHOD FOR BLADDER CANCER

CROSS REFERENCE TO RELATED APPLICATIONS

This application is a U.S. National Phase filing under 35 U.S.C. § 371 of International Application PCT/JP2021/029360, filed Aug. 6, 2021, and published as WO 2022/030626 A1 on Feb. 10, 2022. PCT/JP2021/029360 claims priority from Japanese application number 2020-133478, filed Aug. 6, 2020. The entire contents of each of these prior applications are hereby incorporated herein by reference.

TECHNICAL FIELD

The present invention relates to detection of cancer cell-specific extracellular vesicles (medium/large extracellular vesicles) in the urine of bladder cancer patients, and a diagnosis method for bladder cancer using the same.

BACKGROUND ART

Cancers, which have been recognized as a leading cause of death in Japan since the 1980s, is one of the leading causes of death worldwide. Despite advances in medical diagnostic and therapeutic techniques, it is still difficult to say that diagnostic and therapeutic methods have been fully established. Among them, bladder cancer is diagnosed in more than an estimated hundreds of thousands of cases worldwide each year, and 20,000 cases are newly diagnosed in Japan. Approximately one-third of them are thought to be potentially invasive or metastatic at the time of diagnosis, and highest morbidity and mortality among various urinary tract cancers (renal pelvis, ureter, bladder)(Non-patent literature 1).

Bladder cancer is caused by cancerous transformation of the bladder tissue including the urothelium, and histologically, urothelial carcinoma accounts for 90% of all cases. And 70% of these cases are superficial and noninvasive. Approximately 75% of patients diagnosed with transitional cell carcinoma present with superficial tumors that can be treated by transurethral resection. The recurrence rate of superficial tumor disease exceeds 60%, and less than 30% of recurrent bladder tumors progress to invasive tumor disease (Non-patent literature 2). Therefore, in addition to the importance of early detection of patients with or suspected of having bladder cancer, lifelong surveillance is important for successful treatment.

The majority of patients with bladder cancer seek medical attention after presenting with gross or microscopic hematuria or other worrisome urinary symptoms such as urinary frequency and dysuria. However, no method exists to accurately and easily identify the presence of early-stage bladder cancer, and definitive diagnosis of bladder cancer requires a combination of procedures.

Urinary cytology, the microscopic examination of cells from urine samples, may be used as initial screening. Urinary cytology can examine detached cells for the presence of specific cell surface antigens, nuclear morphology, gene expression or other biological markers, and is useful in cases of high-grade malignancies, but the sensitivity to detect other low-grade tumors is low, and there is a constraint (Non-patent literature 3). Regarding the accuracy of urinary cytology, the extent to which bladder cancer cells are released into the urine varies greatly depending on the timing of urine sampling and disease activity, and there is a problem that the interpretation of the results cannot deny the element of subjectivity, and the judgment results may fluctuate. Therefore, cytology is not ideal for bladder cancer screening and surveillance.

The most reliable definitive diagnosis for patients with the above symptoms and suspected bladder cancer are cystoscopy under local or general anesthesia, followed by solid tissue biopsy if necessary. However, the above symptoms often originate from diseases such as urinary tract infections or benign prostatic hyperplasia, and such invasive and burdensome examinations must be performed even in patients who do not have bladder cancer. Therefore, there is a demand for tests using highly accurate biomarkers for less invasive screening applications.

Commonly known methods for measuring tumor markers for urinary system cancer include NMP22 (Nuclear Matrix Protein 22), BTA (Bladder Tumor Antigen), cytokeratin 8 and 18, and the like. However, although these methods are relatively more sensitive than cytology, many false positives have been reported (Non-patent literatures 4, 5, and 6).

Therefore, the methods for detecting bladder cancer patients using existing biomarkers are not sufficient as markers for diagnosing bladder cancer, and they do not provide any teaching regarding the application of early diagnosis of bladder cancer. Therefore, a highly sensitive and specific marker for diagnosing bladder cancer that enables early diagnosis of bladder cancer has not yet been found.

In recent years, it has been proposed to use micromembrane fractions separated from cells as a liquid biopsy, which is a non-invasive diagnostic material, to determine the presence or absence of morbidity and disease (Patent literatures 1 and 2). Such micromembrane fractions are broadly classified into exosomes, microvesicles, and the like, depending on their size, and their use is attracting attention. Among them, microvesicle extracellular vesicles are known to play an extremely important role in tumor invasion (Non-patent literature 7), and it has been reported that extracellular vesicles present in urine are associated with diabetic nephropathy, and therefore, their clinical usefulness is expected. (Non-patent literature 5). It has been suggested that extracellular vesicles are abundant in human body fluids compared to circulating tumor cells (CTCs), and that they play an extremely important role in tumor invasion and malignant transformation (Non-patent literatures 7 and 8).

In particular, knowledge has been accumulating about methods for extracting and detecting urinary micromembrane fractions, and for example, it is known that urinary Tamm-Horsfall protein (uromodulin)(hereinafter abbreviated as THP) is contained in large amounts and forms high-molecular polymers. In order to separate these high-molecular polymers and micromembrane fractions, a method of extracting exosomes after decomposing the high-molecular polymers in advance by reduction treatment (Non-patent literature 9), and a method of concentrating microvesicles in healthy human urine and characterizing them with a flow cytometer (Patent literature 3) are known.

CITATION LIST

Patent Literature

[Patent literature 1] JP 5838963 B2
[Patent literature 2] JP 2015-91251 A
[Patent literature 3] JP 2019-215342 A Non-Patent Literature

[Non-patent literature 1] Jemal et al., Cancer statistics. CA Cancer J Clin. 57; 43-66, 2007

[Non-patent literature 2] Zieger et al., Long-term follow-up of noninvasive bladder tumours (stage Ta): recurrence and progression. BJU Int. 85; 824-8, 2000

[Non-patent literature 3] Wiener et al. Accuracy of urinary cytology in the diagnosis of primary and recurrent bladder cancer. Acta Cytol. 37(2); 163-9, 1993

[Non-patent literature 4] Takashi M et al., Bladder cancer marker (urinary BTA, urinary NMP22). Rinsho Kensa Gaido 2001-2002. 945-7, 2001

[Non-patent literature 5] Takashi M et al., Use of diagnostic categories in urinary cytology in comparison with the bladder tumor antigen (BTA) test in bladder cancer patients. Int Urol Nephrol. 31; 189-96, 1999

[Non-patent literature 6] Akaza H et al., Evaluation of Urinary NMP22 (Nuclear Matrix Protein 22) as a Diagnostic Marker for Urothelial Cancer. NMP22 as a Urinary Marker for Surveillance of Bladder Cancer. Japanese Journal of Cancer and Chemotherapy 24; 829-36, 1997

[Non-patent literature 7] James W et al. Regulated delivery of molecular cargo to invasive tumour-derived microvesicles. Nat Commun. 6(6919), 2015

[Non-patent literature 8] Timaner et al. Microparticles from Tumors Exposed to Radiation Promote Immune Evasion in Part by PD-L1. Oncogene 39(1); 187-203, 2020

[Non-patent literature 9] Patricia Fernandez-Llama et al., Tamm-Horsfall protein and urinary exosome isolation. Kidney Int. 77(8); 736-742, 2010

SUMMARY OF INVENTION

Technical Problem

As described above, urine can be a non-invasive and effective clinical test material for testing bladder cancer, but there is no test that is capable of early and accurate diagnosis of bladder cancer using biomarkers contained in urine as indicators. Therefore, in the present invention, we focus on bladder cancer-specific extracellular vesicles contained in the urine, particularly microvesicles with a diameter of 0.1 to 1 m (medium/large extracellular vesicles), and an object of the present invention is to identify the substance present in the urinary microvesicles of bladder cancer patients, and to construct a method of assisting in early and accurate diagnosis of bladder cancer.

The term “extracellular vesicles” as used herein means medium/large extracellular vesicles that do not contain exosomes 100 nm or less, or small extracellular vesicles, and contains microvesicles. Hereinafter, the case of using microvesicles as an example of extracellular vesicles will be described, but the present invention is not limited thereto.

The term “separation” as used herein is used synonymously with fractionation, detection, and the like.

Solution to Problem

As a result of intensive studies aimed at solving the above-mentioned problems, the present inventors were able to identify proteins specifically present in microvesicles in urine collected from bladder cancer patients by shotgun proteomics analysis. Some of the identified proteins were analyzed and the present inventors newly discovered microvesicles that are present specific to bladder cancer and are positive for an anti-human CD66a antibody, an anti-human CD66c antibody, and/or an anti-human CD66e antibody (hereinafter collectively and sometimes referred to as anti-human CD66a/c/e antibodies). Furthermore, by calculating the abundance ratio of these anti-human CD66a/c/e antibody-positive microvesicles, we were able to establish a method that is less invasive and can assist in the early and accurate diagnosis of bladder cancer. Using this method, we verified this method using dozens of patient samples (bladder cancer patients, non-bladder cancer patients, and healthy subjects), and confirmed that CD66a/c/e-positive microvesicles are useful for diagnosis/examination applications of bladder cancer patients. Proteins other than CD66a/c/e identified by shotgun proteomics analysis are also suggested to be useful for diagnosis/examination applications in bladder cancer patients.

The present invention provides:

A method of assisting in diagnosis of bladder cancer, comprising:

[1] enriching microvesicles contained in urine derived from a subject patient, and determining whether or not the subject patient has bladder cancer depending on an amount of a marker protein present in the microvesicles.

[2] The method of [1], characterized in that the amount of the marker protein present in the microvesicles is observed by detecting an amount of at least one marker protein selected from the group consisting of IGHG1, CRABP2, PLG, AHSG, HP, IGHG2, ANXA2, IGHM, SERPINA1, CFB, TF, NME2, C4BPA, A2M, TACSTD2, FGG, C4B, F2, C3, IGHA1, CP, SERPINA3, CA1, CAPN5, APOB, FAM129B, C9, TMSB10, C1QB, IGLC6, IGKC, CEACAM7, UPK3A, CEACAM5, ARHGDIB, SRC, FGB, C1QC, LRG1, UPK3BL, DEFA3, SERPIND1, FN1, SDCBP2, APOA1, ITIH4, AGRN, SERPINF1, PDLIM1, ANXA9, PSCA, HBA1, SLC2A1, ITIH2, CYSRT1, SERPINC1, PGLYRP2, SPRR1A, PROS1, RAB27B, UGDH, MARCKS, EFHD2, APOL1, CD66a, CD66b, CD66c, CGM2, and CD66e present in the microvesicles.

[3] The method of [1] or [2], characterized in that the amount of CD66a, CD66b, CD66c, CGM2, or CD66e present in the microvesicles is observed by calculating a ratio (A/B) of microvesicles (A) expressing CD66a, CD66b, CD66c, CGM2, and CD66e with respect to microvesicles (B) expressing CD10, CD13, and CD26.

[4] The method of [1] or [2], characterized in that the amount of CD66a, CD66b, CD66c, CGM2, or CD66e present in the microvesicles is observed by calculating a ratio (A/C) of microvesicles (A) expressing CD66a, CD66b, CD66c, CGM2, and CD66e with respect to microvesicles (C) expressing CD10, CD13, CD26, and MUC1.

[5] The method of any one of [1] to [4], wherein a higher amount or ratio of the marker protein present in urinary microvesicles derived from the subject patient compared to an amount or ratio of the marker protein present in urinary microvesicles derived from a control indicates that the subject patient has bladder cancer.

[6] A method of assisting in determining whether or not a subject patient has bladder cancer, comprising:

measuring an amount of CD66a/b/c/e or CGM2 present in urinary microvesicles, and determining that the biological sample is derived from a patient with bladder cancer when the measured amount of CD66a/b/c/e or CGM2 is high compared to a control.

[7] The method of any one of [1] to [6], for observing progress of bladder cancer treatment, or for deciding a therapeutic effect of bladder cancer, by comparing an amount of protein present in a first sample taken from a subject patient and an amount of protein present in a second sample taken from the subject patient after a treatment period.

[8] The method of any one of [1] to [7], further comprising correlating as indicative of superficial bladder cancer, invasive stage 1 bladder cancer, or invasive stage 2-3 bladder cancer The present invention includes:

a method of diagnosing bladder cancer, comprising measuring (detecting) a marker protein present in microvesicles;

a method of measuring (detecting) a marker protein present in microvesicles for diagnosis of bladder cancer;

an in vitro method of diagnosing bladder cancer, characterized by measuring (detecting) a marker protein present in microvesicles;

use of an antibody capable of detecting a marker protein present in microvesicles for manufacturing a kit for diagnosis of bladder cancer; and a method of measuring (detecting) a marker protein present in microvesicles to provide information necessary for diagnosing bladder cancer.

Advantageous Effects of Invention

By simply and specifically separating and observing microvesicles specifically present in the urine of bladder cancer patients, which is the method of the present invention, it is possible to assist in early and accurate diagnosis of bladder cancer with low invasiveness for first-time patients.

In addition, in the monitoring of the prognosis (presence or absence of metastasis) after treatment such as surgery and chemotherapy in bladder cancer patients, improvement of diagnostic performance (improvement of clinical sensitivity, and reduction of oversight) compared to tests using conventional urinary cytology is expected. It is also expected that observation using the fractions obtained by the present invention will enable estimation of diseases, drug administration effects, or other medical conditions in subjects.

BRIEF DESCRIPTION OF THE DRAWINGS

FIG. 1 is a histogram of the particle size distribution of a fraction extracted from a bladder cancer patient, as measured by scattered light and fluorescence NTA.

FIG. 2 is a histogram of the particle size distribution of a fraction extracted from a healthy subject, as measured by scattered light and fluorescence NTA.

FIG. 3 is a graph showing the particle diameters corresponding to 10%, 50%, and 90% of the particles, when fractions extracted from healthy subjects and bladder cancer patients were measured by scattered light and fluorescence NTA.

FIG. 4 is a Venn diagram showing the number of proteins detected by analyzing microvesicle fractions extracted from pooled samples of bladder cancer patients and healthy subjects by shotgun proteomics.

FIG. 5 is a table showing the results of enrichment analysis of 585 proteins detected only in bladder cancer patients. Those in light font (regulated exocytosis, Hemostasis, and Transport of small molecules in the Description column) were also detected in a similar analysis of healthy subjects.

FIG. 6 is a graph obtained by performing principal component analysis on the basis of each result of bladder cancer patients and healthy subjects, and shows up to the second principal component.

FIG. 7 is a graph obtained by performing OPLS-DA analysis on the basis of each result of bladder cancer patients and healthy subjects.

FIG. 8 is a heat map showing the quantification results of proteins measured by performing shotgun proteomics analysis on enriched microvesicle fractions (bladder cancer patients and healthy subjects) for each patient.

FIG. 9 is a heat map showing the profile of all detected CEACAM family (CD66) proteins among the proteins shown in FIG. 8.

FIG. 10 is a figure estimating the size of observed CD66a/c/e-positive microvesicles in the urine of bladder cancer patients by developing the microvesicles by size verification beads of side scattered light (SSC) and a histogram.

FIG. 11 (upper) shows flow cytometry observed images of urinary microvesicles stained with anti-human CD66a, anti-human CD66c, and anti-human CD66e antibodies from bladder cancer patients, and FIG. 11 (lower) is a graph showing percentages of CD66c or CD66e and percentages of merged extracellular vesicles when CD66a is set as 100%.

FIG. 12 shows flow cytometry observed images of urinary microvesicles stained with anti-human CD66b and anti-human CD66a/c/e antibodies from bladder cancer patients.

FIG. 13 shows flow cytometry observed images of urinary microvesicles stained with an anti-human CD66a/c/e antibody from bladder cancer patients, non-bladder cancer patients, and healthy subjects.

FIG. 14 is an explanatory diagram showing a method for targeting CD66a/c/e-positive microvesicles. This is a gating method of flow cytometry that selects only CD66a/c/e-positive microvesicles from observation of the entire image.

FIG. 15 is a figure of flow cytometry obtained by developing MUC1-positive (CD66a/c/e-negative), multipeptidase-positive (CD10, CD13, and CD26-positive, CD66a/c/e-negative), and CD66a/c/e-positive microvesicles in the entire image of micromembrane fraction in observed image by Annexin5 and side scattered light.

FIG. 16 is a figure explaining that the CD66a/c/e-positive microvesicle fraction in bladder cancer patients is different from multipeptidase-positive (CD10, CD13, and CD26-positive) microvesicles.

FIG. 17 The CD66a/c/e-positive microvesicle fraction in bladder cancer patients is also positive for MUC1. FIG. 17 is a figure explaining that the CD66a/c/e-positive microvesicles are secreted from cancerous urothelial cells which were originally normal.

FIG. 19 is a graph showing the results of percentage comparison of the CD66a/c/e-positive fraction and the multipeptidase-positive fraction in flow cytometry observed images (10 bladder cancer patients, 4 non-bladder cancer patients, and 9 healthy subjects).

FIG. 20 is a graph showing the results of comparison of the ratio of the CD66a/c/e-positive fraction to the multipeptidase-positive fraction, and the ratio of the CD66a/c/e-positive fraction to the combined multipeptidase-positive fraction and MUC1-positive fraction (10 bladder cancer patients, 4 non-bladder cancer patients, and 9 healthy subjects).

FIG. 21 is a figure showing the results of negative and positive graphs and ROC analysis between bladder cancer patients and other patients, using the CD66a/c/e-positive fraction alone, the ratio of the CD66a/c/e-positive fraction to the multipeptidase-positive fraction, and the ratio of the CD66a/c/e-positive fraction to the combined multipeptidase-positive fraction and MUC1-positive fraction.

FIG. 22 shows the cut-off lines of the point (the top of ROC analysis) where sensitivity and specificity are well-balanced and diagnostic performance is best, with respect to the CD66a/c/e-positive fraction alone, the ratio of the CD66a/c/e-positive fraction to the multipeptidase-positive fraction, and the ratio of the CD66a/c/e-positive fraction to the combined multipeptidase-positive fraction and MUC1-positive fraction.

FIG. 23 shows a microvesicle enrichment method using a sample volume of 10 mL, and shows that the number of CD66a/c/e-positive fraction that can be detected in this case can be increased compared to a sample volume of 0.8 mL.

FIG. 24 is a figure comparing the results of urinary cytology (negative and positive judgments) and the judgment results of the method of the present invention. A urine sample that was negative for bladder cancer by urinary cytology can be positively judged using the method of the present invention to detect the presence of cancer.

DESCRIPTION OF EMBODIMENTS

Figure 18:
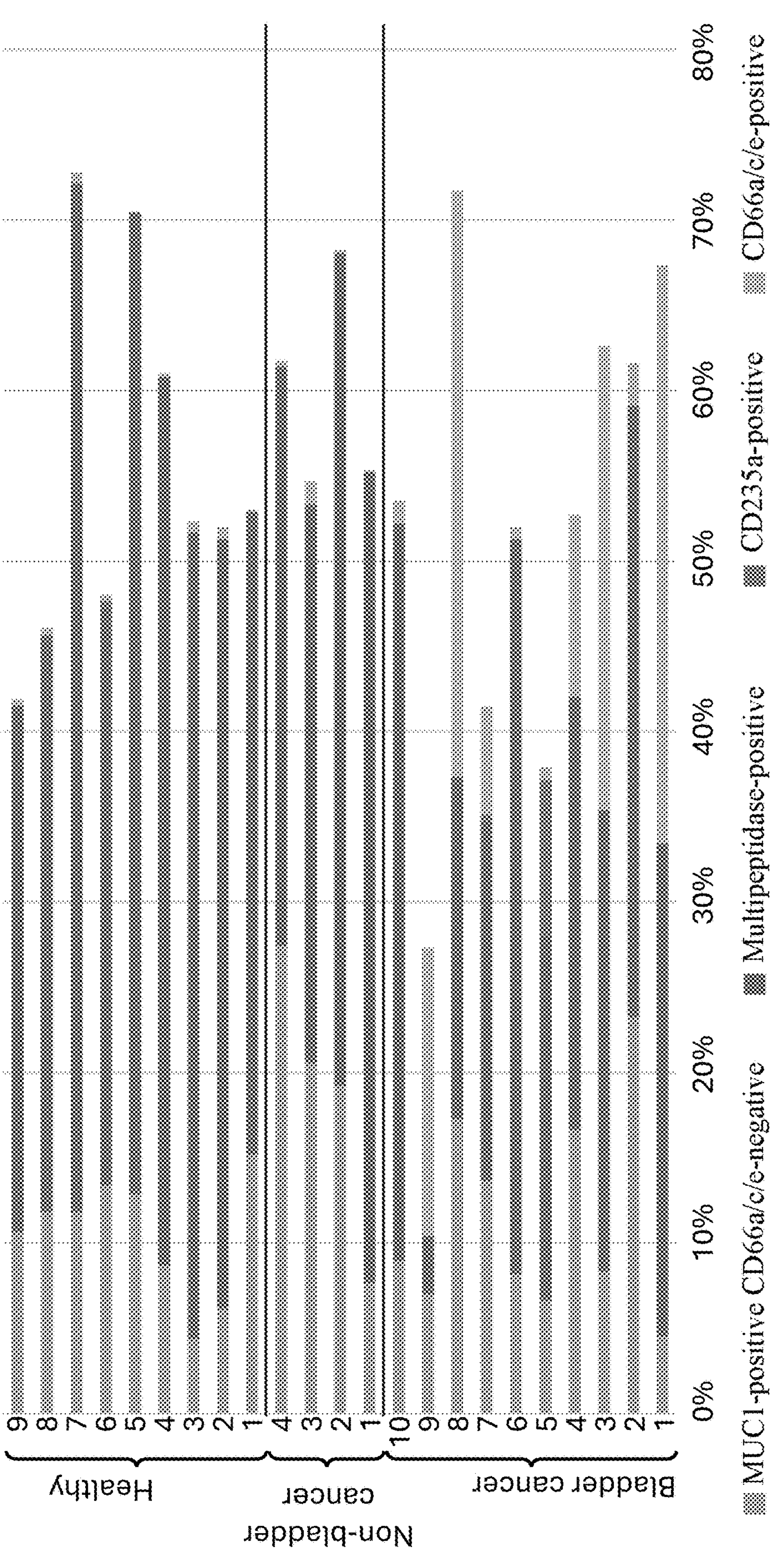
FIG. 18 is a graph showing a list of all microvesicles observed by a flow cytometer in bladder cancer patients, non-bladder cancer patients, and healthy subjects (percentage of each fraction in the entire observed image).

Embodiments of the present invention will be described in detail below, but embodiments of use are not limited thereto.

The present invention is a method of assisting in early and accurate diagnosis of bladder cancer using cancer cell-specific microvesicles that are present in the urine of bladder cancer patients and positive for anti-human CD66a/c/e antibodies. The cancer cell-specific microvesicles that are positive for anti-human CD66a/c/e antibodies can be characterized by two features, a substance that recognizes human CD66a/c/e and a particle size of approximately 0.1 to 1 μm in diameter called microvesicles. "Pretreatment" as used herein includes enrichment and collection, which are sometimes used almost synonymously.

"Urine" as used herein may be collected urine as it is, or may be dissolved or suspended in water, acidic solution, alkaline solution, buffer solution, or the like, and used after further treatment if desired. Acidic solutions, alkaline solutions, and buffer solutions that can be used in the present invention can be appropriately selected and used by those skilled in the art.

Hereinafter, an example of conditions for isolating and observing cancer cell-specific microvesicles that are positive for anti-human CD66a/c/e antibodies using a flow cytometer and application to diagnostic methods will be described, but the present invention is not limited thereto.

The pretreatment method for removing contaminants and enriching microvesicles that can be used in the present invention is characterized by centrifugation. For example, with reference to the method described in JP 2019-215342 A, it can be carried out according to the following steps.

The collected urine specimen is subjected to low-speed centrifugation to separate cell fractions, debris, and the like, and the supernatant is collected (step 1). Conditions such as low-speed centrifugation can be carried out according to known methods, and a supernatant obtained by centrifugation at 2,000×g for 20 minutes at room temperature can be used.

A step of collecting a supernatant by further centrifuging the supernatant obtained in step 1 at low speed may be carried out. This centrifugation step is preferable because it can precipitate platelet-derived vesicles, apoptotic blisters, and the like. As in step 1, the supernatant obtained by centrifugation at 2,000×g for 20 minutes at room temperature can be collected and used.

The supernatant obtained in step 1 is centrifuged at high speed to precipitate a microvesicle fraction (step 2). As the conditions for this step, for example, a precipitate obtained by centrifugation at 20,000×g for 30 minutes at room temperature can be used.

A buffer solution containing a reducing agent (for example, 1,4-dithiothreitol (DTT), Tris(2-carboxyethyl) phosphine hydrochloride: TCEP) is added to the precipitated fraction obtained in step 2 and allowed to stand (step 3). By carrying out this step, the disulfide bonds in a THP polymer can be reductively cleaved and the THP polymer can be degraded.

The sample added with the reducing agent in step 3 is centrifuged at high speed to enrich the microvesicles and remove the reducing agent (step 4). This high-speed centrifugation can enrich the microvesicle fraction and remove contaminants. As the conditions for this step, a precipitate obtained by centrifugation at 20,000×g for 30 minutes at room temperature can be used. This step 4 can be repeated, if desired. It is preferable to carry out high-speed centrifugation multiple times to remove contaminants and increase the purity of the microvesicles.

Since the reducing agent to be added is added for the purpose of cleaving disulfide bonds, any reducing agent capable of cleaving disulfide bonds may be used. Those skilled in the art can appropriately select and use reagents commonly used as reducing reagents for protecting the SH groups of proteins or cleaving disulfide bonds, such as dithiothreitol, 2-mercaptoethanol, 2-mercaptoethylamine hydrochloride, Tris(2-carboxyethyl)phosphine hydrochloride (TCEP), cysteine hydrochloride, tributylphosphine (TBP), iodoacetamide, glutathione, hydrazine, and the like. Among these reducing agents, those that do not affect the measurement of microvesicles are preferred, and those that do not destabilize the lipid bilayer are more preferred. These reducing agents may be used alone or in combination of two or more.

There are several pretreatment methods that can be used as one aspect of the present invention other than the above steps. For example, a combination of membrane filters with various pore sizes used for filtration and sterilization of aqueous and protein-containing solutions can be used to extract the desired microvesicle fraction. In this case, a method equivalent to Micro-Filtration using pore diameters of 0.1 to 10 μm is suitable.

In addition, a method of separating only target microvesicles using, as a substance that can specifically bind to microvesicles, for example, a substance that can specifically bind to proteins, lipids, or sugars present on the surface may be used.

In addition, other pretreatment methods include an equilibrium density gradient centrifugation method, in which the sample is centrifuged with a density gradient solute; an immunological capture method, in which antibodies specific to surface antigens of a micromembrane fraction are used, and the micromembrane fraction is bound to various carriers and collected; a method of collecting the fraction that elutes earlier than soluble proteins by size exclusion chromatography (gel filtration method); a phospholipid affinity method using carriers that bind to membrane constituting components of a micromembrane fraction in the presence of metal ions; a polymer precipitation method, in which a high-molecular-weight polymer and a micromembrane fraction are mixed to precipitate the desired micromembrane fraction; and the like. Those skilled in the art can appropriately select and carry out these methods, but even in these methods, by performing the step of adding a reducing agent to the sample, it can be performed as an alternative method to steps 1 to 4 above.

Hereinafter, samples obtained by enriching urine and removing contaminants by these methods are referred to as treated urine specimens.

Next, an example of observation conditions for a flow cytometer specialized for microvesicles will be explained, but the present invention is not limited thereto.

The flow cytometer that can be used in the present invention is not limited to a specific device, and any flow cytometer that employs a flow cell such as a quartz cuvette system or a jet-in-air system can be used.

An observation method using a flow cytometer that can be used in the present invention can be carried out, for example, according to the following steps.

(1) Staining of Microvesicles

In this step, a reducing agent is added, and the enriched treated urine sample is mixed with a staining reagent to stain microvesicles (step 5-A). More particularly, microvesicles are stained by mixing a staining reagent, such as a fluorescently-labeled surface antigen-specific antibody, with the treated urine sample. As for the staining method, those skilled in the art can adopt a standard method, and depending on the situation, the conditions can be appropriately examined and carried out. In order to target multiple antigens in microvesicles, multicolor classification may be performed by staining with multiple types of labeled antibodies for detection. For example, Annexin 5, a protein that binds to phosphatidylserine (PS), a membrane constituting component of microvesicles, in the presence of metal ions, can be used.

Other substances that can specifically bind to microvesicles include substances that can bind to proteins, lipids, or sugars present on the surface of microvesicles. The step of reacting the substance capable of binding to the proteins, lipids, or sugars with the microvesicles can be carried out, when characterizing cancer cell-specific microvesicles present in urine, or when characterizing microvesicles derived from normal tissues present in urine.

As proteins present on the surface of urinary microvesicles, for example, CD235a, CD59, CD44, CD33, CD45, CD144, CD66a, CD66b, CD66c, CD66e, CD41, CD61, EP-CAM, CD324, CD14, CD81, CD31, CD274, CD63, Alix, CD105, CD133, CD279, CD15, TSG101, CD20, CD249, CD5, CD10, CD26, CD273, CD9, MUC1, CD13, CD146, CD62E, Annexin 5, or a combination thereof can be used.

For example, as microvesicles contained in the urine from healthy subjects, it is preferable to use a fraction positive for all of CD10, CD13, and CD26, as microvesicles having various types of membrane-type peptidases, and an Annexin5, CD227(MUC1)-positive fraction, as microvesicles derived from epithelial cells, in combination, because it enables more accurate separation.

On the other hand, as microvesicles in the urine from bladder cancer patients, it is preferable to use a fraction positive for CD66a, CD66c, CD66e, and MUC1 on the surface to observe a differential diagnosis, diagnosis, and prognosis of bladder cancer patients.

Substances other than the above that can specifically bind to microvesicles are, for example, substances that have binding affinity for proteins, substrates for enzymes, coenzymes, regulatory factors, substances that specifically bind to receptors, lectins, sugars, glycoproteins, antigens, antibodies or antigen-binding fragments thereof, hormones, neurotransmitters, phospholipid-binding proteins, proteins containing pleckstrin homology (PH) domains, cholesterol-binding proteins, or a combination thereof. The antigen-binding fragment contains an antigen-binding site(s), and may be, for example, a single-domain antibody, Fab, Fab', or scFv.

(2) Addition of IgG

In this step, in order to detect the THP polymer that could not be removed by the reduction treatment in the observation image, fluorescently labeled IgG is mixed and reacted with the THP polymer (step 5-B). Fluorescently labeled IgG is mixed and reacted with the mixture obtained by mixing the treated urine specimen and the staining reagent in the previous step, or the treated urine specimen before mixing with the staining reagent (step 5-B). The origin of the IgG is not particularly limited, and for example, mouse IgG, human IgG, rat IgG, rabbit IgG, goat IgG, bovine IgG, and the like can be used. As with the staining step for microvesicles, those skilled in the art can perform according to standard methods. For example, allophycocyanin (APC)-labeled mouse IgG and Mix-n-Stain APC Antibody Labeling kit (Biotium) can be used according to the standard protocol and allowed to stand at room temperature for 30 minutes.

(3) Flow Cytometer Settings

By adjusting the voltage and threshold of the photomultiplier tube for forward scattered light and side scattered light, the particle group with a specific diameter is focused in the observation area. When setting conditions such as these parameters, it is preferable to measure unstained samples and stained samples and determine the voltage setting and sheath flow rate that satisfy the detection sensitivity for each target.

Flow cytometer parameters can be set appropriately by those skilled in the art by searching for optimal conditions. For example, the flow rate can be set to 12 μL/min, the voltage for forward scattered light can be set to 381, and the voltage for side scattered light can be set to 340, and, for each detection sensitivity, the fluorescence intensity threshold can be set to 200. The wavelength and voltage of the excitation light (Ex.) and fluorescence detection filter (Em.) for each fluorescent substance can be appropriately selected and set according to each fluorescent substance used.

By using the parameters of the flow cytometer set above, the particle size in the observation area is estimated. Measurements can be performed according to standard methods using polystyrene beads of uniform size (for example, SPHERO™ Nano Polystyrene Size Standard Kit, Spherotech) or the like. For estimating the particle size of the observation area, for example, it is preferable that the particle sizes of polystyrene beads are 0.22 m, 0.45 m, 0.88 m, and 1.35 m.

The diameter to be set as the observation area is not particularly limited as long as it is a size that includes microvesicles. For example, the diameter is preferably approximately 1 m or less, more preferably approximately 100 nm to 1 m, and still more preferably approximately 200 nm to 1 m. Especially when observing these microparticles, side scattered light is preferable because it has higher resolution than forward scattered light and can be used for particle size verification.

This step is not limited to the embodiment performed between the above staining step and IgG addition step and the following measurement/separation step. For example, after setting the parameters, the staining step, the IgG addition step, and the measurement/separation step can be performed. Alternatively, once set, a series of steps can be repeated without setting the parameters for each measurement.

(4) Measurement/Separation by Flow Cytometry

Data is obtained using a flow cytometry. When multicolor measurement is performed, the leakage of fluorescence leaking from each fluorescence to a detector other than the assigned detector is corrected, and measurement results are obtained under these conditions (step 6).

(5) Exclusion of Aggregated Microvesicles, and Exclusion of Complexes with IgG-Captured Fraction (Step 6-A)

Microvesicles may aggregate, but in order to exclude aggregated microvesicles from the observation image, it is possible to mark and gate out 1) those whose pulse width value of side scattered light is very high outside the group, and 2) those whose plots of forward scattered light and side scattered light are high outside the group. In particular, it is effective when microvesicles aggregate due to the addition of the pretreatment method.

In addition, in order to remove immune complexes with the IgG-captured fraction, it is possible to mark and gate out positive populations that react with fluorescently labeled IgG. This step is preferable because the positive populations that react with fluorescently labeled IgG can be marked and gated out in order to exclude the THP polymer that could not be completely removed by the reduction treatment from the observation image.

Either the step of excluding aggregated microvesicles or the step of removing immune complexes captured by IgG may be performed first, or both steps may be performed simultaneously. It is possible to select as appropriate according to the environment in which those skilled in the art perform it.

(6) Characterization of Obtained Microvesicle Populations (Step 6-B)

By gating the microvesicles detected by multicolor, it is possible to separate and characterize the microvesicle populations of the cells from which they are derived. This step allows confirmation of the separated microvesicles in the urine.

The present invention enables separation and characterization of urinary microvesicles, and these characterized fractions can be further separated using a cell sorter. It is also possible to observe specific contents (nucleic acids, metabolites, proteins, and lipids) from these separated fractions and apply them clinically. Separated fractions may be further used for frequency analysis of each microvesicle population and expression level analysis of target molecules.

A characterization technique that assists in early and accurate diagnosis of bladder cancer can be performed by combining the particle size of microvesicles and the detection of one or more proteins present on the surface of the microvesicles. Proteins present on the surface of microvesicles can be detected using a single protein or a combination of multiple proteins. For the combination of protein, after confirming each reactivity of urinary microvesicles derived from bladder cancer patients and each reactivity of urinary microvesicles derived from non-bladder cancer (urinary system disease) patients and healthy subjects, the combination of proteins can be identified by narrowing down a combination of proteins with reactivity specific to bladder cancer patients.

Those skilled in the art can appropriately select and carry out a method of searching for markers that can assist in early and accurate diagnosis of bladder cancer by analyzing proteins contained in the enriched microvesicles. For example, it is preferable to identify the markers using techniques such as shotgun proteomics, two-dimensional electrophoresis, mass cytometry, and the like. For example, microvesicles enriched from the urine of bladder cancer patients, non-bladder cancer (urinary system disease) patients, and healthy subjects are observed by immunofluorescent staining, and proteins that are highly abundant only in the urine of bladder cancer patients may be identified. Proteins contained in urinary microvesicles of bladder cancer patients include IGHG1, CRABP2, PLG, AHSG, HP, IGHG2, ANXA2, IGHM, SERPINA1, CFB, TF, NME2, C4BPA, A2M, TACSTD2, FGG, C4B, F2, C3, IGHA1, CP, SERPINA3, CA1, CAPN5, APOB, FAM129B, C9, TMSB10, C1QB, IGLC6, IGKC, CEACAM7, UPK3A, CEACAM5, ARHGDIB, SRC, FGB, C1QC, LRG1, UPK3BL, DEFA3, SERPIND1, FN1, SDCBP2, APOA1, ITIH4, AGRN, SERPINF1, PDLIM1, ANXA9, PSCA, HBA1, SLC2A1, ITIH2, CYSRT1, SERPINC1, PGLYRP2, SPRR1A, PROS1, RAB27B, UGDH, MARCKS, EFHD2, APOL1, and the like, and these can be used as markers derived from bladder cancer patient-specific microvesicles. These markers can be used alone, or multiple types of markers can be used in combination. The use of the combination of multiple types is expected to improve detection accuracy specific to bladder cancer patients, and is therefore preferred.

In particular, microvesicles positive for at least one of CD66a, CD66c, or CD66e (preferably two or more of CD66a, CD66c, or CD66e, most preferably CD66a, CD66c, and CD66e) as the proteins that are abundantly present only in the urine of bladder cancer patients may be extracted and preferably used, but they are not limited thereto.

Diagnostic accuracy can be improved by identifying and excluding proteins that exhibit reactivity specific to urinary microvesicles derived from non-bladder cancer (urinary system disease) patients and healthy subjects. As such proteins, microvesicles thought to originate from renal tubules, such as microvesicles positive for at least one of CD10, CD13, or CD26 (preferably two or more of CD10, CD13, or CD26, most preferably CD10, CD13, and CD26) (in addition, more preferably CD66a, CD66c, and CD66e negative), may be used as microvesicles contained in the urine of healthy subjects. For example, the diagnostic accuracy can be significantly improved by calculating the ratio (A/B) of microvesicles (A) positive for CD66a, CD66c, and/or CD66e (most preferably CD66a, CD66c, and CD66e-positive) to microvesicles (B) positive for CD10, CD13, and/or CD26 (most preferably CD10, CD13, and CD26-positive)(in addition, more preferably CD66a, CD66c, and CD66e negative).

As used herein, for example, microvesicles positive for CD66a, CD66c, and/or CD66e mean microvesicles positive for at least one of CD66a, CD66c, or CD66e, or microvesicles positive for two or more of CD66a, CD66c, or CD66e, or microvesicles positive for CD66a, CD66c, and CD66e.

In addition to the CD10, CD13, CD26-positive microvesicle population described above, CD227 (MUC1)-positive microvesicles may be extracted and used in combination with the above proteins. MUC1-positive microvesicles are thought to be derived from urothelial cells, and it is preferable to extract the MUC1-positive microvesicles and use them in combination with the CD10, CD13, CD26-positive microvesicles in order to extract microvesicle populations to be excluded, because accuracy is improved. For example, the diagnostic accuracy can be significantly improved by calculating the ratio (A/C) of microvesicles (A) positive for CD66a, CD66c, and/or CD66e (most preferably CD66a, CD66c, and CD66e-positive) to microvesicles (C) positive for CD10, CD13, CD26, and/or MUC1 (most preferably CD10, CD13, CD26, and MUC1-positive)(in addition, more preferably CD66a, CD66c, and CD66e negative).

When samples derived from patients with symptoms of hematuria are used, blood-derived microvesicles may be mixed, and the ratio of CD66a/c/e-positive microvesicles and multipeptidase-positive microvesicles may decrease. Therefore, in such cases, corrections may be made to judge whether they are true cancer cell-derived microvesicles in flow cytometry observation images. Such correction is preferable because the diagnostic assistance of the present invention can be performed with high accuracy. For correction, for example, microvesicles positive for CD235a (Glycoprotein A) expressed in human erythrocytes and erythroid progenitor cells can be used.

In addition, those skilled in the art can set appropriate criteria, such as setting criteria for determining an appropriate combination.

A device used for carrying out the present invention is not particularly limited as long as they are capable of accurately observing particle sizes suitable for microvesicles and capable of measuring specific surface antigens. For example, JVC Kenwood's ExoCounter (JVC Kenwood) can be used. ExoCounter performs surface antigen-specific sandwich detection of exosomes with discs and antibody nanobeads. Particle size can be characterized by limiting the size to that which fits within the grooves (260 nm) on the disc surface. This is preferable because exosomes in body fluid samples can be directly measured without the need for isolation and purification step.

In addition to the above, as a measurement technique that can separate and observe microvesicles, for example, NanoSight, a nano-tracking particle size measuring device (NanoSight, Malvern Panalytical) can be used in combination of NTA (Nano Tracking Analysis) technology and FFF (Field Flow Fractionation) technology. With the NTA technology, the Brownian motion of nanoparticles in liquid can be observed in real time on a PC screen, and with the FFF technology, separation takes place in a thin flow channel. Due to the special geometry of the channel, the flow forms a laminar flow with a radial cross-section, and since perpendicular to this laminar flow produces a separating force that separates small particles such as microvesicles by size, more accurate separation and observation are expected. By combining such separation/observation methods with surface antigens that characterize individual microvesicles, microvesicles can be characterized, organ specificity and disease specificity can be enhanced, and clinical applications can be achieved.

As a different embodiment of the present invention, it can also be used as a method for monitoring disease progression in a subject and as a method for monitoring disease recurrence in an individual. These methods include a profiling step of observing substances contained in the microvesicles in addition to the step of separating microvesicles from urine specimens. Observing profiles in contents subjects with a particular medical condition can be used, for example, to estimate the presence of a particular disease. For example, by appropriately setting the sampling period for separating microvesicles according to the detection of the target disease, it is possible to obtain a more detailed profile, observe the condition, and assist diagnosis. It can also be used as a method of monitoring disease status after drug administration.

According to the present invention, since microvesicles can be effectively used as materials for clinical examination, microvesicles present in urine can be easily and specifically extracted and observed, and surface antigens present on membranes can be used to characterize individual microvesicles (what cells, tissues, and organs they are derived from). As a result, it is expected that the value of the test will increase as a diagnostic and test application that focuses on specific organs, tissues, and cells that match specific diseases. In addition, by observing using the fractions obtained by the present invention, it becomes possible to estimate diseases, drug administration effects, or other medical conditions in subjects.

EXAMPLES

The present invention will now be further illustrated by, but is by no means limited to, the following Examples.

Example 1: Enrichment of Microvesicles from Urine of Human Bladder Cancer Patients Less than 10 mL of urine was collected from healthy subjects and bladder cancer patients. The urine samples were centrifuged at 2,330×g for 10 minutes at 20° C. to obtain urine supernatants. The supernatants were centrifuged at approximately 2,330×g for 10 minutes at approximately 20° C. to obtain supernatants from which urinary lipids, cellular debris, blood-derived components, and the like were removed, and the supernatants were used for the following experiments.

An 800 μL aliquot was taken from each of the obtained urine and centrifuged at 18,900×g for 30 minutes at 20° C. The supernatant was removed from the centrifuged product to enrich the microvesicle fraction in the pellet. To the pellet, 180 μL of phosphate-buffered saline (PBS) containing dithiothreitol (DTT) at a final concentration of 10 mg/mL was added. After stirring with a vortex, it was allowed to stand at 37° C. for 10 minutes. After standing, it was centrifuged at 18,900×g for 30 minutes at 20° C. From the centrifuged product, the microvesicle fraction was enriched in the pellet.

Example 2: Particle Measurement of Extracted Fractions by Nanoparticle Analysis System To each pellet in which the microvesicle fraction was enriched by the same treatment as in Example 1 (except for using 10 mL of urine), 100 μL of PBS was added. All samples were further diluted 3-fold, and measured using Nanosight NS300 (Malvern Panalytical). The observation conditions of the device are shown in Table 1 (scattered light measurement) and Table 2 (fluorescence measurement). In addition, extracellular vesicles labeled with ExoGlow-NTA Dye (System Biosciences), which specifically binds to intact extracellular vesicle membranes, were also measured by fluorescence NTA (Nano Tracking Analysis). FIGS. 1 and 2 show particle size distribution histograms of fractions extracted from healthy subjects and bladder cancer patients, as measured by scattered light and fluorescence NTA. The diameters corresponding to 10%, 50%, and 90% of the total number of particles observed by scattered light NTA in eight healthy subjects and eight bladder cancer patients were also shown (FIG. 3). In this enrichment operation, fractions with a diameter of 1 m or more were rarely included, and the main fraction was distributed in the 200-300 nm diameter range. In addition, some of these fractions contained cell membranes (10%-60%), which were considered to be "medium extracellular vesicles (: microvesicles)" according to their size. Furthermore, it was confirmed that there were no differences in the particle size distribution of the extracted extracellular vesicle fractions between healthy subjects and bladder cancer patients.

TABLE 1

| Scattered light measurement | |
|---|---|
| Camera | sCMOS |
| Laser Type | Blue488 |
| Camera Level | 13 |
| Slider Shutter | 1232 |
| Slider Gain | 219 |
| Frames per Second | 25.00 |
| Number of Frames | 1498 |
| Temperature | 26.5° C. |
| Viscosity | Water 0.86 |
| Syringe pump Speed | 80 |
| Detect Threshold | 5 |
| Blur Size | Auto |
| Max Jump Distance | Auto |

TABLE 2

| Fluorescence measurement | |
|---|---|
| Camera | sCMOS |
| Laser Type | Blue488 |
| Camera Level | 16 |
| Slider Shutter | 1300 |
| Slider Gain | 512 |
| Frames per Second | 25.00 |
| Number of Frames | 1498 |
| Temperature | 26.5° C. |
| Viscosity | Water 0.86 |
| Syringe pump Speed | 80 |
| Detect Threshold | 5 |
| Blur Size | Auto |
| Max Jump Distance | Auto |
| Filter Wheel | 500 nm |

Example 3: Proteins Detected in Enriched Microvesicle Fractions by Shotgun Proteomic Analysis A. Extraction of Protein Fractions from Enriched Microvesicle Fractions Obtained by Pretreatment of Urine In order to identify proteins specifically present in microvesicles in the urine of bladder cancer patients, urine from four bladder cancer patients (patient 1: Tis, urinary cytology class III, patient 2: T2, urinary cytology class V, patient 3: T2, urinary cytology class V, patient 4: Ta, urinary cytology class II) and four healthy subjects were used to enrich the microvesicle fractions by the same way as in Example 1. Two sets of fractions were prepared: one set was two mixed pools obtained by mixing samples from four patients and four healthy subjects for each group, with the equivalent amount per patient after protein quantification, and the other set was microvesicle fractions individually extracted from each patient and healthy subject.

In order to efficiently extract, in particular, membrane proteins from the fraction in which the microvesicle fraction was enriched, a protein solubilization method using PTS (Phase Transfer Surfactant) was carried out. "MPEX PTS Reagents for MS" (GL Science Inc.) was used as a reagent kit using this principle. To each pellet in which the microvesicle fraction was enriched in Example 1, 250 μL of Reagent B of the kit was added, the mixture was sonicated (power: MAX) with an ultrasonic homogenizer (Bioruptor: Sonicbio Co., Ltd.) at 10° C. for 10 cycles of 1 minute and 30 seconds at intervals of 30 seconds. After disruption, the mixture was enriched by repeating 14,000 g×15 minutes twice with a centrifugal filter (Amicon ultra 3K, Merck). This fraction was subjected to protein quantification by BCA assay (using Piercem BCA Protein Assay kit (Thermo Fisher Scientific Inc.)).

B. Enzymatic Digestion of Protein Fractions

Each fraction that had been quantified by BCA assay was dissolved in Reagent B above to a concentration of 7 μg/30 μL to prepare a sample for membrane protein digestion. To each sample, 1.5 μL of 100 mmol/L dithiothreitol (DTT) was added (for reductive cleavage of disulfide bonds) and incubated at room temperature for 30 minutes. Further, 1.5 μL of 550 mmol/L iodoacetamide was added (for carbamidomethylation of Cys) and incubated at room temperature for 30 minutes in the dark. To the mixture, 116 μL of reagent A of the kit above was added, and 1.5 μL of trypsin (TPCK-Trypsin (Thermo Fisher Scientific Inc.: Prod #20233)) was added. Protein digestion was carried out by incubating overnight at room temperature. To the mixture, 150 μL of reagent C and 1.5 μL of reagent D were added. After addition, the mixture was vortexed for 1 minute and centrifuged at 25° C. and 15,600×g for 2 minutes to separate the two phases. Since unnecessary solubilizing agent came to the upper phase, it was removed by aspiration with a pipette. In order to remove remaining reagent C, after centrifugal enrichment, 50 μL of 5% acetonitrile and 0.1% trifluoroacetic acid (TFA) were added and vortexed.

C. Desalting and Enrichment of Peptides

GL-Tip SDB (GL Science Inc) was used for desalting and enriching each enzymatic digestion product above. Each chip was first conditioned by adding 20 μL of 80% acetonitrile and 0.1% TFA aqueous solution and centrifuging at 3,000×g for 2 minutes at room temperature. To this, L of 5% acetonitrile and 0.1% TFA aqueous solution was added and centrifuged at 3,000×g for 2 minutes at room temperature to equilibrate the column. The entire amount of each sample obtained in the procedure of Example 3B was added to the chip, and this was centrifuged at 3,000×g for 5 minutes at room temperature to adsorb peptides on the column. To this, 20 μL of 5% acetonitrile and 0.1% TFA aqueous solution was added and centrifuge at 3,000×g for 2 minutes at room temperature to wash the column, and then, 50 μL of 80% acetonitrile and 0.1% TFA aqueous solution was added and centrifuged at 3,000×g for 2 minutes at room temperature to elute peptides. The peptide-containing solution was once dried in a miVac centrifugal evaporator and suspended in L of 0.1% formic acid/2% acetonitrile aqueous solution.

D. Mass Spectrometry Measurement

LC-MS/MS analysis was performed on the above samples using a Fourier transform type Orbitrap mass spectrometer (Q-Exactive: Thermo Fisher Scientific Inc.) connected to a nano-LC system (EASY-nLC1000: Thermo Fisher Scientific Inc.), and 5 μL of the sample for mass spectrometry measurement prepared above was used for measurement. Acclaim$^{RT}$PepMap100 (Thermo Fisher Scientific Inc.: C18, packing material diameter 3 m, inner diameter 75 m, and column length 2 cm) as the trap column, and Acclaim$^{RT}$-PepMapRSLC (Thermo Fisher Scientific Inc.: C18, packing material diameter 2 m, inner diameter 50 m, and column length 15 cm) as the analytical column were used. Measurement was carried out under the following conditions: Mobile phase A was 0.1% formic acid aqueous solution, mobile phase B was 0.1% formic acid/acetonitrile, flow rate was 200 nL/min, and gradient was 0-40% mobile phase B/for 200 minutes, 40-100% mobile phase B/for 10 minutes, and 100% mobile phase B/for 10 minutes.

Full MS/dd-MS2 mode was used as the scanning condition for MS measurement, and after scanning Full MS, MS/MS spectra of high-intensity signals were acquired. Table 3 shows the setting conditions.

TABLE 3

| General | |
|---|---|
| Polarity | positive |
| Default charge state | 2 |
| **Full MS** | |
| scan range | 350 to 1400 m/z |
| Resolution | 70000 |
| AGC target | 3E+06 |
| Maximum IT | 50 ms |
| **dd-MS2** | |
| Resolution | 35000 |
| AGC target | 1E+05 |
| Maximum IT | 100 ms |
| Loop count | 20 |
| TopN | 20 |
| Isolation window | 4.0 m/z |
| Fixed first mass | 100.0 m/z |
| NCE/stepped NCE | 32 |

E. Data Analysis

Proteome Discoverer 1.4 software (Thermo Fisher Scientific Inc.) was used for database searches of the obtained data. The database search was carried out by the SequestHT algorithm using *Homo sapiens* taxonomy catalogued in the UniProt database (UP000005640; Oct. 18, 2020). Table 4 shows the search conditions for SequestHT.

TABLE 4

| Input Data | |
|---|---|
| Protein Database | *Homo_sapiens*_Uniprot_201210.fast |
| Enzyme Name | Trypsin (Full) |
| **Tolerances** | |
| Precursor Mass Tolerance | 10 ppm |
| Fragment Mass Tolerance | 0.6 Da |
| **Dynamic Modification** | |
| N-Terminal Modification | Carbamidomethyl/+57.021 Da |
| 1. Dynamic Modification | Oxidation/+15.995 Da (M) |
| 2. Dynamic Modification | Carbamyl/+43.006 Da (K, R) |
| **Static Modification** | |
| 1. Static Modification | Carbamidomethyl/+57.021 Da (C) |

The obtained MS/MS data were further subjected to LFQ (label-free quantification) analysis using the MaxQuant platform (version 1.6.6.0). Database searches were carried out using the same UniProt database as described above. Protein and peptide identification was undertaken under the following conditions: false discovery rate of 0.01, minimum number of peptides required for protein identification of 1, minimum score of 40 for modified peptides, and no lower limit for unmodified peptides.

In order to make a rough comparison of proteins contained in urinary microvesicles of bladder cancer patients and healthy subjects, mixed pools obtained by mixing samples from four patients and four healthy subjects for each group, with the equivalent amount per patient after protein quantification, were analyzed. The proteins detected in each of the two groups were selected from the Proteome Discoverer search results with a score of 1.0 or higher. Regarding the patient pool and the healthy subject pool, a list of proteins detected by shotgun proteomics analysis of the extracted microvesicle fraction is shown in FIG. 4 and Table 5 (patients: 1334 proteins, and healthy subjects: 1393 proteins). In addition, enrichment analysis using Metascape (Tripathi et al., Cell Host & Microbe (2015), 18: 723-735) was carried out on the proteins detected in bladder cancer patients only (585 proteins), among the proteins detected in each pool. The result is shown in FIG. 5. There were some functional categories related to cell adhesion, which is a characteristic of cancer, but, as the most frequently categorized functions of proteins, ribosome-related functional categories (protein complex, translation), including eukaryotic translation elongation and ribonucleoprotein complex assembly RNA, were calculated. This could be one feature of the proteins contained in microvesicles derived from cancer patients.

Next, microvesicles individually extracted from 4 patients with bladder cancer (patient 1: Tis, urinary cytology class III, patient 2: T2, urinary cytology class V, patient 3: T2, urinary cytology class V, patient 4: Ta, urinary cytology class II) and 4 healthy subjects were analyzed. The obtained MS/MS data were subjected to LFQ (label-free quantification) analysis using the MaxQuant platform, and quantitative results for each patient were calculated. The following statistical analyses were performed using these. MetaboAnalyst 5.0 was used for statistical analyses. Principal component analysis was performed on the results of 4 bladder cancer patients and 4 healthy subjects, and a graph showing up to the second principal component is shown in FIG. 6. Although patient 2 had a slightly different profile from the other 3 patients, there was a trend toward some degree of protein profile difference detected between the groups of 4 bladder cancer patients and 4 healthy subjects. Therefore, OPLS-DA analysis, which allows discriminant analysis between groups, was performed. As for the evaluation of the model obtained by OPLS-DA, the closer $R^2Y$ and $Q^2Y$ are to 1, the better the model is (It is considered a good model if $R^2Y$ is 0.65 or more and $Q^2Y$ is 0.5 or more). In the score plot shown in FIG. 7, $R^2X=0.253$, $R^2Y=0.847$, and $Q^2Y=0.608$. Since $R^2Y$ and $Q^2Y$ were good, the patient group and the healthy group were significantly discriminated. Next, s-plot analysis was performed for the purpose of estimating the important components (proteins) for discriminating between the two groups. The components important for discrimination were judged from p[1] and p[corr], and proteins with p[1] of 0.05 or more and p[corr] of 0.6 or more were extracted as important components for discrimination. A list of these extracted proteins is shown in Table 5, and a heat map was created using these (FIG. 8).

The heat map shown in FIG. 8 visualizes each numerical value (2 to −2) obtained by shading of red (2 to 0) and blue (0 to −2). Each numerical value before visualization is shown in Table 6-1 (corresponding to the upper half of FIG. 8) and Table 6-2 (corresponding to the lower half of FIG. 8).

TABLE 5

| Genenames | p[1] | p(corr)[1] |
|---|---|---|
| IGHG1 | 19.74 | 0.94 |
| CRABP2 | 14.60 | 0.91 |
| PLG | 13.61 | 0.89 |
| AHSG | 13.77 | 0.89 |
| HP | 13.86 | 0.89 |
| IGHG2 | 18.38 | 0.89 |
| ANXA2 | 7.79 | 0.88 |
| IGHM | 13.20 | 0.88 |
| SERPINA1 | 16.19 | 0.86 |
| CFB | 18.03 | 0.86 |
| TF | 13.50 | 0.86 |
| NME2 | 5.79 | 0.85 |
| C4BPA | 15.65 | 0.85 |
| A2M | 15.78 | 0.84 |
| TACSTD2 | 13.25 | 0.84 |
| FGG | 16.29 | 0.83 |
| C4B | 17.97 | 0.83 |
| F2 | 14.86 | 0.82 |
| C3 | 19.04 | 0.82 |
| IGHA1 | 13.69 | 0.81 |
| CP | 14.91 | 0.81 |
| SERPINA3 | 12.53 | 0.81 |
| CA1 | 8.68 | 0.80 |
| CAPN5 | 6.39 | 0.79 |
| APOB | 15.02 | 0.78 |
| FAM129B | 8.23 | 0.77 |
| C9 | 14.94 | 0.76 |
| TMSB10 | 9.56 | 0.74 |
| C1QB | 10.18 | 0.74 |
| IGLC6 | 12.72 | 0.74 |
| IGKC | 10.89 | 0.73 |
| CEACAM7 | 10.48 | 0.73 |
| UPK3A | 9.77 | 0.73 |

TABLE 5-continued

| Genenames | p[1] | p(corr)[1] |
|---|---|---|
| CEACAM5 | 11.10 | 0.72 |
| ARHGDIB | 10.12 | 0.71 |
| SRC | 5.11 | 0.71 |
| FGB | 9.75 | 0.70 |
| C1QC | 11.83 | 0.70 |
| LRG1 | 10.85 | 0.69 |
| UPK3BL | 9.32 | 0.69 |
| DEFA3 | 9.12 | 0.69 |
| SERPIND1 | 11.23 | 0.68 |
| FN1 | 11.27 | 0.67 |
| SDCBP2 | 9.76 | 0.66 |
| APOA1 | 9.56 | 0.66 |
| ITIH4 | 9.93 | 0.66 |
| AGRN | 8.84 | 0.66 |
| SERPINF1 | 10.03 | 0.65 |
| PDLIM1 | 9.02 | 0.65 |
| ANXA9 | 9.02 | 0.65 |
| PSCA | 7.17 | 0.65 |
| HBA1 | 11.13 | 0.64 |
| SLC2A1 | 11.18 | 0.63 |
| ITIH2 | 11.84 | 0.62 |
| CYSRT1 | 6.24 | 0.61 |
| SERPINC1 | 8.89 | 0.61 |
| PGLYRP2 | 6.27 | 0.61 |
| SPRR1A | 6.15 | 0.61 |
| PROS1 | 6.20 | 0.61 |
| RAB27B | 6.39 | 0.60 |
| UGDH | 8.00 | 0.60 |
| MARCKS | 6.34 | 0.60 |
| EFHD2 | 6.42 | 0.60 |
| APOL1 | 6.23 | 0.60 |

TABLE 6-1

| C | C | C | C | P | | ? | p | class |
|---|---|---|---|---|---|---|---|---|
| −0.32 | −0.32 | −0.32 | −0.32 | −0.32 | 0.87 | 1.04 | −0.32 | CYSRT1 |
| −0.32 | −0.32 | −0.32 | −0.32 | −0.32 | 1.08 | 0.85 | −0.32 | PGLYRP2 |
| −0.33 | −0.33 | −0.33 | −0.33 | −0.33 | 1.15 | 0.81 | −0.33 | RAB27B |
| −0.33 | −0.33 | −0.33 | −0.33 | −0.33 | 1.17 | 0.8 | −0.33 | EFHD2 |
| −0.69 | −0.69 | 0.17 | −0.69 | 0.39 | 1.17 | 1.04 | −0.69 | PDLIM1 |
| −0.69 | −0.69 | 0.17 | −0.69 | 0.39 | 1.17 | 1.03 | −0.69 | ANXA9 |
| −0.58 | −0.58 | −0.58 | −0.58 | 0.19 | 1.82 | 0.87 | −0.58 | LRG1 |
| −0.5 | −0.5 | −0.5 | −0.5 | 0.38 | 1.65 | 0.48 | −0.5 | UPK3BL |
| −0.21 | −0.96 | −0.96 | −0.96 | 0.39 | 1.2 | 1.26 | 0.26 | CRABP2 |
| −0.16 | 0.29 | −1.09 | −1.09 | 0.6 | 0.72 | 0.78 | −0.05 | TMSB10 |
| 0.21 | −0.15 | −1.05 | −1.05 | 0.19 | 0.68 | 1.23 | −0.07 | UPK3A |
| −0.21 | −1.33 | 0.29 | −0.25 | 0.03 | 0.41 | 0.85 | 0.21 | PSCA |
| −0.32 | −0.62 | −0.01 | −0.39 | 0.19 | 0.33 | 0.87 | −0.04 | CAPN5 |
| −0.51 | −0.51 | −0.51 | −0.51 | 0.37 | 0.3 | 1.89 | −0.51 | SDCBP2 |
| −0.54 | −0.54 | −0.54 | −0.54 | 0.94 | −0.54 | 0.32 | 1.46 | FGB |
| −0.26 | −0.2 | −0.31 | −0.49 | 0.43 | −0.02 | 0.22 | 0.64 | NME2 |
| −0.74 | −0.74 | −0.74 | −0.74 | 1.23 | 0.02 | 0.24 | 1.45 | TACSTD2 |
| −0.9 | −0.9 | −0.9 | −0.9 | 1.28 | −0.28 | 0.72 | 1.88 | FGG |
| −0.12 | −1.21 | 0.36 | −1.42 | 0.65 | 0.35 | −0.28 | 1.68 | HBA1 |
| −0.63 | −0.63 | −0.63 | −0.63 | 1.02 | 0.05 | −0.63 | 2.09 | SLC2A1 |
| 0.24 | −0.67 | −0.67 | −0.67 | 0.58 | 0.63 | −0.67 | 1.23 | UGDH |
| −0.78 | −0.16 | −0.78 | −0.78 | −0.08 | −0.78 | 1.19 | 2.19 | ITIH2 |
| −0.54 | −0.54 | −0.54 | −0.54 | 0.26 | −0.54 | 0.54 | 1.89 | ITIH4 |
| −0.63 | −0.63 | −0.63 | −0.63 | 0.08 | −0.63 | 1.3 | 1.77 | C1QC |
| −0.6 | −0.6 | −0.6 | −0.6 | 0.13 | −0.6 | 0.97 | 1.91 | SERPIND1 |
| −0.6 | −0.6 | −0.6 | −0.6 | 0.12 | −0.6 | 0.94 | 1.96 | FN1 |
| −1.3 | −0.55 | −1.3 | −0.75 | 0.4 | −0.04 | 1.27 | 2.27 | C4B |
| −1.73 | −0.41 | −0.79 | −1.21 | 0.95 | −0.3 | 1.27 | 2.22 | C3 |
| −0.54 | −0.54 | −0.54 | −0.54 | 0.33 | −0.54 | 1.32 | 1.07 | C1QB |
| −0.84 | −0.84 | −0.84 | −0.84 | 0.37 | −0.19 | 1.44 | 1.73 | C4BPA |
| −0.85 | −0.85 | −0.85 | −0.85 | 0.38 | −0.2 | 1.42 | 1.79 | A2M |
| −0.11 | −1.4 | −0.38 | −0.2 | 0.39 | −0.3 | 0.48 | 1.53 | APOA1 |
| Healthy 1 | Healthy 4 | Healthy 2 | Healthy 3 | Patient 3 | Patient 4 | Patient 1 | Patient 2 | |

TABLE 6-2

| C | C | C | C | P | P | P | P | class |
|---|---|---|---|---|---|---|---|---|
| 0.11 | −1.32 | −0.36 | −0.54 | −0.24 | 0.11 | 0.48 | 1.76 | SERPINF1 |
| −0.82 | −0.82 | −0.82 | −0.82 | 0.54 | −0.2 | 0.59 | 2.34 | APOB |
| −0.96 | −0.96 | −0.35 | −0.96 | 0.38 | −0.04 | 0.47 | 2.43 | C9 |
| −0.71 | −0.71 | −0.71 | −0.71 | 0.09 | 0.33 | 0.78 | 1.62 | IGHM |
| −0.53 | −1.11 | −1.11 | −1.11 | 0.29 | 0.09 | 1.33 | 2.15 | CFB |
| −0.56 | −1.22 | −0.13 | −1.22 | −0.03 | 0.21 | 1.2 | 1.74 | F2 |
| −0.38 | −0.28 | −0.24 | −0.81 | −0.23 | 0.14 | 0.7 | 1.1 | FAMI29B |
| −0.32 | −0.32 | −0.32 | −0.32 | −0.32 | −0.32 | 0.84 | 1.1 | APOL1 |
| −0.33 | −0.33 | −0.33 | −0.33 | −0.33 | −0.33 | 1.13 | 0.82 | MARCKS |
| −0.32 | −0.32 | −0.32 | −0.32 | −0.32 | −0.32 | 1.03 | 0.87 | SPRRIA |
| −0.32 | −0.32 | −0.32 | −0.32 | −0.32 | −0.32 | 1.06 | 0.86 | PROSI |
| −0.54 | −0.54 | −0.54 | −0.54 | −0.54 | 0.3 | 1.67 | 0.72 | CEACAM7 |
| −0.57 | −0.57 | −0.57 | −0.57 | −0.57 | 0.21 | 1.83 | 0.8 | CBACAM5 |
| 0.12 | −0.73 | −0.73 | −0.73 | −0.73 | 0.97 | 1.01 | 0.8 | ARHGDIB |
| −0.99 | −0.73 | −0.97 | −0.24 | 0.27 | 0.41 | 1.41 | 0.85 | PLG |
| 0.24 | −0.69 | −0.69 | −0.69 | −0.69 | 0.14 | 0.81 | 1.54 | SERPINC1 |
| −0.94 | −0.94 | −0.94 | −0.17 | 0.11 | 0.53 | 1.25 | 1.1 | HP |
| −0.69 | −0.69 | −0.69 | 0.21 | −0.69 | 0.54 | 0.92 | 1.09 | AGRN |
| −0.97 | −0.41 | −1.67 | 0.27 | −0.13 | 1.35 | 0.82 | 0.73 | IGLC6 |
| −1.19 | −0.28 | −0.95 | 0.09 | −0.46 | 0.9 | 1.07 | 0.82 | IOKC |
| −0.74 | −0.4 | −0.24 | −1.51 | 0.28 | 0.68 | 1.28 | 0.65 | AHSG |
| −0.74 | −0.04 | −0.17 | −0.71 | 0.29 | 0.33 | 0.54 | 0.52 | ANXA2 |
| −1.14 | 0.07 | −0.44 | −1.43 | 0.91 | 0.54 | 0.51 | 0.97 | TF |
| −0.78 | −0.5 | 0.15 | 0 | 0.25 | 0.3 | 0.41 | 0.16 | SRC |
| −1.45 | −0.3 | −0.13 | −0.13 | 0.22 | 1.11 | −0.11 | 0.8 | DEFA3 |
| −1.58 | −0.12 | −0.51 | −0.93 | −0.42 | 1.11 | 1.26 | 1.19 | CP |
| −1.48 | −0.39 | −0.07 | −0.71 | 0.04 | 0.44 | 1.46 | 0.72 | SERPINA3 |
| −1.02 | −0.47 | −0.93 | −1 | −0.27 | 0.67 | 1.24 | 1.78 | SERPINA1 |
| −0.45 | −0.45 | −0.45 | −0.45 | −0.45 | 0.66 | 0.7 | 0.89 | CA1 |
| −1.53 | −0.82 | −0.1 | −0.47 | −0.21 | 1.05 | 0.75 | 1.33 | IGHAI |
| −1.22 | −1.35 | −0.73 | −0.96 | 0.37 | 1.18 | 0.9 | 1.8 | IGHGI |
| −1.3 | −0.72 | −0.57 | −1.3 | −0.12 | 1.65 | 0.79 | 1.58 | IGHG2 |
| Healthy 1 | Healthy 4 | Healthy 2 | Healthy 3 | Patient 3 | Patient 4 | Patient 1 | Patient 2 | |

The proteins shown in Table 5 include proteins that have been suggested to be associated with bladder cancer (UPK3A, PSCA, SRC, and the like). In the future, it is suggested that these proteins will be useful in utilizing extracellular vesicles as biomarkers in the urine of bladder cancer patients. In addition, CEACAM5 and CEACAM7 were included in the extracted proteins with high scores, suggesting that the CEACAM family (CD66) proteins are the above candidate proteins. Furthermore, the profile of all detected CEACAM family (CD66) proteins was illustrated in a heat map in the patient group and the healthy group (FIG. 9).

The heat map shown in FIG. 9 visualizes each numerical value (2 to −2) obtained by shading of red (2 to 0) and blue (0 to −2). Each numerical value before visualization is shown in Table 7.

TABLE 7

| P | P | P | P | C | C | C | C | class |
|---|---|---|---|---|---|---|---|---|
| −0.35 | 2.47 | −0.35 | −0.35 | −0.35 | −0.35 | −0.35 | −0.35 | CBACAM8 |
| 1.85 | −1.09 | 0.79 | 0.47 | −1.09 | −0.11 | −0.42 | −0.39 | CEACAM1 |
| 2.47 | −0.35 | −0.35 | −0.35 | −0.35 | −0.35 | −0.35 | −0.35 | CEACAM6 |
| 2.29 | 0.51 | −0.55 | −0.07 | −0.55 | −0.55 | −0.55 | −0.55 | CEACAM5 |
| 2.24 | 0.55 | −0.57 | 0.08 | −0.57 | −0.57 | −0.57 | −0.57 | CEACAM7 |
| Patient 1 | Patient 2 | Patient 3 | Patient 4 | Healthy 1 | Healthy 3 | Healthy 2 | Healthy 4 | |

The CEACAM family proteins that could be detected were CEACAM1 (CD66a), CEACAM5 (CD66e), CEACAM6 (CD66c), CEACAM7 (CGM2), and CEACAM8 (CD66b). The expression profiles of these CEACAM proteins differ from patient to patient, and from the viewpoint of detecting bladder cancer patients with high sensitivity, it was thought that a form that detects a combination of several CEACAM proteins in microvesicles would be suitable.

Proteins detected by shotgun proteomics analysis may be used as surface markers to characterize bladder cancer urinary microvesicles, or for clinical examination and diagnosis by using their contents as biomarkers.

Example 4: Observation of Microvesicles in the Urine of Bladder Cancer Patients Using a Flow Cytometer A. Immunofluorescent Staining of Microvesicles Enriched from Urine To the pellet obtained by enriching the microvesicle fraction in Example 1, 60 μL of PBS was added, and the microvesicle fraction was dispersed in the solution by vortexing. To this solution, 1 μL of each of FITC-Annexin5 (Becton Dickinson Biosciences), APC/Cy7anti-human CD10 (Biolegend), Brilliant Violet421anti-human CD13 (Biolegend), PEanti-human CD26 (Biolegend), PerCP/Cy5.5anti-human CD66a/c/e (Biolegend), PerCPanti-human CD66b (Biolegend), Anti-Human CEACAM-1/CD66a Alexa Fluor 488 Antibody (R&D), Anti-Human CEACAM-6/CD66c Alexa Fluor 750 Antibody (R&D), Anti-Human CEACAM-5/CD66e Alexa Fluor 405 Antibody (R&D), Brilliant Violet421anti-humanCD66a/c/e(Biolegend), PE/Cy7anti-human CD227 MUC1(Biolegend), APC/Cy7anti-human CD235a(Biolegend), and APC labeled mouse IgG (purchased Normal Mouse IgG (Wako) was labeled according to the standard protocol attached to Mix-n-Stain APC Antibody Labeling kit (Biotium)) was added and allowed to stand at room temperature for 30 minutes.

B. Observation of Urinary Microvesicles Using a Flow Cytometer

The measurement was performed using a BD FACS-Verse™ (Becton Dickinson and Company) as a flow cytometer. The measurement procedure and parameter settings are as follows. As samples, each fluorescently stained fraction prepared in the above Example 4A was suspended in 750 μL of 10 mmol/L Hepes (pH 7.4), 0.14 mol/L NaCl, and 2.5 mmol/L $CaCl_2$. The flow rate was set to 12 μL/min, the voltage for forward scattered light was set to 381, the voltage for side scattered light was set to 340, and the threshold for each was set to 200. The wavelengths of the excitation light (Ex.) and fluorescence detection filter (Em.) and the voltage for each fluorescent substance were FITC: Ex. 488 nm, Em. 527/32 nm, and voltage 442, PE: Ex. 488 nm, Em. 586/42 nm, and voltage 411, PerCP: Ex. 488 nm, Em. 700/54 nm, and Voltage 556, PE/Cy7: Ex. 488 nm, Em. 783/56 nm, and voltage 564.3, APC: Ex. 640 nm, Em. 660/10 nm, and voltage 538.2, APC/Cy7: Ex. 640 nm, Em. 783/56 nm, and voltage 584.8, and Brilliant Violet421: Ex. 405 nm, Em. 448/45 nm, and voltage 538.2. In order to estimate the particle size in the observation area, uniform-sized polystyrene beads (SPHERO™ Nano Polystyrene Size Standard Kit, Spherotech) were measured. Polystyrene beads with particle diameters of 0.25 m, 0.45 m, 0.79 m, and 1.34 m were used. The observation target was mainly where the observed particle size converged to 1 m or less at the side scattered light (SSC) intensity (approximately 5.0×e04 or less)(FIG. 10).

C. CD66a, c, e-Positive Microvesicles Present in the Urine of Bladder Cancer Patients Antibodies that specifically recognize CD66a, c, e (CEACAM1, 6, 5), respectively, were used to determine whether the CEACAM proteins detected by shotgun proteomics analysis exist in the same microvesicles or in different microvesicles. The results are shown in FIG. 11. Urine samples from 9 bladder cancer patients were analyzed using the flow cytometer method described above. In patient 2-1, microvesicles positive for CD66a, c, and e, respectively, almost merged with microvesicles positive for other antigens, respectively. From this patient, the presence of microvesicles expressing three kinds of antigens simultaneously on their surface was confirmed. In patients 2-8, many microvesicles positive only for CD66a were observed. The positive rate for each individual antigen of CD66a, c, and e, and the rate in which positivity for each antigen is merged are shown in a graph of the results of 9 patients (FIG. 11). From these results, it can be inferred that a variety of CD66a, c, and/or e-positive microvesicles are contained depending on the patient. It is suggested that there are microvesicles that are positive only for CD66a, c, and e, respectively, and microvesicles that have two or three types of these antigens present at the same time.

D. Microvesicles with Surface Antigen CD66b (CEACAM8)

CD66b (CEACAM8) detected by the shotgun proteomics analysis was also analyzed using a flow cytometer. The results are shown in FIG. 12. In patient 2, in whom CEACAM8 was detected by shotgun analysis, CD66b (CEACAM8)-positive microvesicles were also observed by flow cytometer analysis. In these microvesicles, since a population that merged with CD66a/c/e was observed, it is thought that either antigen is simultaneously expressed.

E. CD66a/c/e-Positive Microvesicles Abundantly Present Only in the Urine of Bladder Cancer Patients Microvesicles enriched from urine by the above method were observed with a flow cytometer. From the results obtained so far, since many microvesicles containing CD66a, c, e (CEACAM1, 6, 5) as major molecules were observed in the patient's urine, we determined that a diagnostic system using an antibody that simultaneously recognizes these antigens would be appropriate, and analysis was performed using a flow cytometer in the detection system using a CD66a/c/e-recognition antibody. Observation of microvesicles in urine from bladder cancer patients, non-bladder cancer (urinary system disease) patients, and healthy subjects revealed that a large number of CD66a/c/e-positive microvesicles were observed only in the urine of bladder cancer patients (FIG. 13). This suggests that CD66a/c/e-positive microvesicles may be useful as a diagnostic marker using urine from bladder cancer patients.

Example 5: Characterization of Microvesicles in the Urine of Bladder Cancer Patients Using a Flow Cytometer A. Targeting of CD66a/c/e-Positive Microvesicles (FIG. 14)

In the observed images, microvesicles were aggregated and multiple aggregated particles were observed (a population in which all surface antigens stained with various stains were positive populations). In order to remove the multiple aggregated particles from the observed image, we prepared an observed image developed by the pulse width (vertical axis) and the pulse area (horizontal axis) in the side scattered light, and excluded populations that greatly deviated from the observed image. Next, the APC-positive population, that is, the mouse IgG population that can be captured by the residual THP polymer, was extracted from the developed view of the side scattered light and APC mouse IgG, and the APC-positive population was extracted and excluded from the observed image. Furthermore, CD10 and CD13-positive populations, which are abundant in healthy subject's urine, were excluded (CD10 and CD13-negative populations were gated in), and CD66a/c/e-positive populations were selected (FIG. 14).

B. Overall Image of Microvesicles in Observed Images (FIG. 15)

From a developed view of CD10 and CD13, a CD66a/c/e-negative and both CD10 and CD13-positive population was extracted, and then, a CD26-positive population were further selected. This population was defined as CD10, CD13, and CD26-positive microvesicles. CD10, CD13, and CD26 are thought to be derived from renal tubules, and the CD10, CD13, and CD26-positive microvesicles can be used as microvesicles contained in healthy subject's urine. Furthermore, a CD66a/c/e-negative and CD227 (MUC1)-positive population was selected. This population was defined as MUC1-positive microvesicles. FIG. 15 shows an example in which the CD66a/c/e-positive microvesicles, the CD10, CD13, and CD26-positive microvesicles, and the MUC1-positive microvesicles were characterized and superimposed on a developed view of side scattered light and Annexin5.

C. Characterization of CD66a/c/e-Positive Microvesicles (FIG. 16, FIG. 17)

Regarding CD66a/c/e-positive microvesicles, it is clear from a developed view of CD66a/c/e and CD26 that CD66a/c/e-positive microvesicles are different from CD10, CD13, CD26-positive microvesicles (FIG. 16). In addition, a developed view of CD66a/c/e and MUC1 shows that CD66a/c/e-positive microvesicles may be MUC1-positive microvesicles (FIG. 17). However, in the urine of bladder cancer patients, CD66a/c/e-negative may be positive for MUC1, similar to those in healthy subjects. As mentioned in Non-patent literature, Igami et al., 2020. Characterization and function of medium and large extracellular vesicles from plasma and urine by surface antigens and Annexin V. PeerJ Analytical Chemistry 2:e4 doi.org/10.7717/peerj-achem.4, CD10, CD13, CD26-positive microvesicles are likely derived from renal tubules, and MUC1-positive microvesicles are likely derived from urothelial cells. There is possibility that CD66a/c/e-positive microvesicles are originally derived from urothelial cells that have become cancerous, and secreted as microvesicles with antigenic CD66a/c/e on their surfaces.

Example 6: Percentage of Each Microvesicle Observed in Urine from 10 Bladder Cancer Patients, 4 Non-Bladder Cancer (Urinary System Disease) Patients, and 9 Healthy Subject Based on the above results, a method of enriching microvesicles in urine and observing microvesicle fractions with different cell origins by a flow cytometer, using proteins on the surface of individual microvesicles has been established. Specifically, the microvesicles are four types of microvesicles with a diameter of 1 m or less, which are positive for MUC1 (CD66a/c/e-negative), positive for multipeptidase (CD10, CD13, CD26-positive, CD66a/c/e-negative), positive for CD235a (erythrocyte-derived microvesicles, hematuria-derived, CD66a/c/e-negative), and positive for CD66a/c/e, respectively. FIG. 18 shows the ratio (%) of these four types of microvesicles observed in the urine of 10 bladder cancer patients, 4 non-bladder cancer (urinary system disease) patients, and 9 healthy subjects, with respect to the entire observed image. Regarding bladder cancer patients, non-bladder cancer patients, and healthy subjects, the ratio (%) of CD66a/c/e-positive microvesicles with respect to the entire observation image were compared (FIG. 19). The number of CD66a/c/e-positive microvesicles was significantly increased in bladder cancer patients compared to non-bladder cancer patients and healthy subjects. In addition, the number of multipeptidase-positive microvesicles was significantly decreased in bladder cancer patients compared to the other two groups (FIG. 19).

Example 7: Effect of a Diagnostic Index that Combines the Ratio of CD66a/c/e-Positive, MUC1-Positive, and Multipeptidase-Positive Microvesicles to Total Since CD66a/c/e-positive microvesicles appear specifically in the urine of cancer patients, the degree of increase can be a direct diagnostic index. On the other hand, MUC1-positive (CD66a/c/e-negative) microvesicles and multipeptidase-positive (CD10, CD13, CD26-positive, CD66a/c/e-negative) microvesicles tend to decrease in the urine of cancer patients over the entire observed image. This result may become a more accurate diagnostic index by incorporating the respective ratios and differences. Actually, when the ratio (A/B) of the CD66a/c/e-positive fraction (A) to the multipeptidase-positive fraction (B), and the ratio (A/C) of the CD66a/c/e-positive fraction (A) to the combined multipeptidase-positive fraction and MUC1-positive fraction (C) were quantified and compared between healthy subjects, non-bladder cancer, and bladder cancer, a significant difference was confirmed in each (FIG. 20). In addition, when divided into bladder cancer patients and others (non-bladder cancer patients and healthy subjects), and 1) CD66a/c/e alone (A), 2) the ratio (A/B) of the CD66a/c/e-positive fraction (A) to the multipeptidase-positive fraction (B), and 3) the ratio (A/C) of the CD66a/c/e-positive fraction (A) to the combined multipeptidase-positive fraction and MUC1-positive fraction (C) were evaluated by ROC curves, as for the AUC value, 3) the ratio of the CD66a/c/e-positive fraction to the combined multipeptidase-positive fraction and MUC1-positive fraction was the highest (FIG. 21). These results suggest that combining CD66a/c/e-positive microvesicles in the observed image of the urine of bladder cancer patients with other microvesicles commonly found in healthy subjects may provide a more accurate diagnostic index. For each pattern of 1) CD66a/c/e alone, 2) the ratio of the CD66a/c/e-positive fraction to the multipeptidase-positive fraction, and 3) the ratio of the CD66a/c/e-positive fraction to the combined multipeptidase-positive fraction and MUC1-positive fraction, from the viewpoint of both sensitivity and specificity, the best cut-off lines were demonstrated together with actual numerical graphs obtained from healthy subjects and bladder cancer patients (FIG. 22). Each cut-off line is the same as the cut-off value used when judging the test results shown in (lower part of FIG. 21).

Example 8: Example of a Simple Pretreatment Measurement Method Using a Larger Volume of Urine Urinary volume of 10 mL or more can often be secured when collecting urine from bladder cancer patients, and by using all of this as test material, the density of microvesicles to be detected can be increased, which is advantageous in performing the test. As a urine pretreatment operation, a microvesicle fraction was extracted from 10 mL of urine volume using a centrifugal filtration device (FIG. 23-1). The benefits in testing are demonstrated by comparing microvesicle fractions extracted from 10 mL and 0.8 mL. FIG. 23-2 shows observed images for each fraction with the same observation time on the flow cytometer. When the flow rate of the flow cytometer was set to 12 μL/min, it took 10 seconds to align 10,000 particles in the observed image with the 10 mL urine volume extraction fraction. When the 0.8 mL urine volume extraction fraction was observed under the same conditions, only about 200 particles could be observed in 10 seconds (FIG. 23-2). From these results, it is possible "to shorten the inspection time". Furthermore, since the number of particles dissolved in the final buffer solution is large in the 10 mL urine volume extraction fraction, it is possible to increase the scale of the whole image of particles to be observed to some extent within an appropriate observation time in testing. FIG. 23-3 shows an example when the number of particles in the entire observed image is 100,000. In order to align 100,000 particles, we were able to observe them in about 1 minute under the conditions described above. In the 0.8 mL urine volume extraction, the number of the CD66a/c/e-positive fraction was 68 when the number in the entire observed image was 10,000, whereas the number of the CD66a/c/e-positive fraction was 269 when the number in the entire observed image was 100,000 (FIG. 23-3). Even if the urine volume is changed, it does not affect the ratio of the positive fraction to the entire observed image, and therefore, when the positive fraction is the target unit of a measurement system that detects the particle concentration or the like of a positive fraction, an increase in the number of target particles is thought to lead to an improvement in sensitivity.

Example 9: Comparative Study of Urinary Cytology and the Method of the Present Invention Using Urine from Bladder Cancer Patients For 20 urine specimens from 20 bladder cancer patients, the results of urinary cytology (classes 2-5) were compared with the percentages of the CD66a/c/e-positive fraction to total in the same specimen, respectively. A cut-off value of 0.81% was used for the CD66a/c/e-positive fraction as described above. The breakdown of urinary cytology results of 20 urine specimens from bladder cancer patients was (class 2: 5 cases, class 3: 4 cases, class 4: 2 cases, class 5: 9 cases). Class 3 is a diagnosis in which the judgement is pending and the existence of a malignant tumor cannot be determined, and class 2 is a diagnosis in which there is no suspicion of malignancy. By using the method of the present invention, 8 cases out of 9 cases with class 2 or 3 by the urinary cytology results were judged as positive. In addition to the conventional examination, the utilization of the method of the present invention, and the usefulness of examination application by the method of the present invention alone are suggested (FIG. 24).

INDUSTRIAL APPLICABILITY

In the present invention, by focusing on CD66a/c/e-positive microvesicles in urine and utilizing them in various measurement methods, a bladder cancer examination can be dramatically improved with better diagnostic performance compared with current urinary cytology and cystoscopy. In other words, it is a non-invasive diagnosis using urine, and although it is non-invasive, it has the potential to surpass the clinical sensitivity of urinary cytology, which has a clinical sensitivity of about 40% (often overlooked). In actual clinical situations, it is thought that this test is effective in diagnosing the presence or absence of bladder cancer using the urine of first-time patients, and in monitoring the prognosis (presence or absence of metastasis) after treatment such as surgery or chemotherapy in bladder cancer patients. In addition, microvesicles contained in urine other than CD66a/c/e-positive urinary microvesicles (MUC1-positive microvesicles and multipeptidase-positive microvesicles) can also improve the diagnostic accuracy of the bladder cancer examination by utilizing their quantitative parameters, and a multi-assay that can measure these simultaneously is useful in actual examinations.

In addition, according to the present invention, depending on the urine collection conditions, a large amount of urine can be subjected to the examination conditions, and taking advantage of urine as a test sample (a large amount of urine can be collected non-invasively from a patient), it is possible to perform examinations with higher accuracy.

In the future, by a simpler method that can define the particle size, CD66a/c/e-positive microvesicles are utilized, and early detection of cancer; prevention that enables day-to-day management of individuals transitioning from healthy to pre-disease state; health checkup or other clinical applications as a predictive marker; are also conceivable. The clinical application value as micromembrane fractions can be enhanced by combining them with other biomarkers contained in urine.

The invention claimed is:

1. A method of diagnosing bladder cancer, comprising:

enriching microvesicles contained in urine derived from a subject patient, wherein said microvesicles have a diameter in the range of 200 nm to 1 μm;

detecting an amount of a marker protein present in said microvesicles; and determining whether or not the subject patient has bladder cancer depending on the amount of said marker protein present in said microvesicles;

wherein said marker protein is CD66a.

2. The method according to claim 1, further comprising detecting an amount of at least one further marker protein present in said microvesicles, wherein said at least one further marker protein is selected from the group consisting of CD66b, CD66c, CGM2, and CD66e.

3. The method according to claim 2, wherein the amount of CD66a, CD66b, CD66c, CGM2, or CD66e present in the microvesicles is observed by calculating a ratio (A/B) of microvesicles (A) expressing CD66a, CD66b, CD66c, CGM2, or CD66e with respect to microvesicles (B) expressing CD10, CD13, or CD26.

4. The method according to claim 2, wherein the amount of CD66a, CD66b, CD66c, CGM2, or CD66e present in the microvesicles is observed by calculating a ratio (A/C) of microvesicles (A) expressing CD66a, CD66b, CD66c, CGM2, or CD66e with respect to microvesicles (C) expressing CD10, CD13, CD26, or MUC1.

5. The method according to claim 1, wherein a higher amount or ratio of the marker protein present in urinary microvesicles derived from the subject patient compared to an amount or ratio of the marker protein present in urinary microvesicles derived from a control indicates that the subject patient has bladder cancer.

6. A method of determining whether or not a subject patient has bladder cancer, comprising:

measuring an amount of CD66a present in urinary microvesicles, wherein said urinary microvesicles have a diameter in the range of 200 nm to 1 μm, and determining that a biological sample is derived from a patient with bladder cancer when a measured amount of CD66a is high compared to a control.

7. The method according to claim 1, for observing progress of bladder cancer treatment, or for deciding a therapeutic effect against bladder cancer, by comparing an amount of said marker protein present in a first sample taken from a subject patient and an amount of said marker protein present in a second sample taken from the subject patient, wherein said second sample is taken from the subject patient after a treatment period.

8. The method according to claim 1, further comprising correlating the amount of CD66a as indicative of superficial bladder cancer, invasive stage 1 bladder cancer, or invasive stage 2-3 bladder cancer.

* * * * *